US010058697B2

(12) United States Patent
Xu et al.

(10) Patent No.: US 10,058,697 B2
(45) Date of Patent: Aug. 28, 2018

(54) THERMOFORMED ELECTRODE ARRAYS

(71) Applicant: Advanced Bionics AG, Staefa (CH)

(72) Inventors: Bing Xu, Valencia, CA (US); Kurt J. Koester, Los Angeles, CA (US); Mark B. Downing, Valencia, CA (US)

(73) Assignee: Advanced Bionics AG, Staefa (CH)

(*) Notice: Subject to any disclaimer, the term of this patent is extended or adjusted under 35 U.S.C. 154(b) by 0 days.

(21) Appl. No.: 14/911,683

(22) PCT Filed: Aug. 27, 2013

(86) PCT No.: PCT/US2013/056875
§ 371 (c)(1),
(2) Date: Feb. 11, 2016

(87) PCT Pub. No.: WO2015/030734
PCT Pub. Date: Mar. 5, 2015

(65) Prior Publication Data
US 2016/0193460 A1    Jul. 7, 2016

(51) Int. Cl.
A61N 1/05        (2006.01)
B29C 51/02       (2006.01)

(52) U.S. Cl.
CPC ............ A61N 1/0541 (2013.01); B29C 51/02 (2013.01)

(58) Field of Classification Search
CPC ............................... A61N 1/0541; B29C 51/02
See application file for complete search history.

(56) References Cited

U.S. PATENT DOCUMENTS

| 3,752,939 | A | 8/1973 | Bartz |
| 4,261,372 | A | 4/1981 | Hansen |
| 4,284,085 | A | 8/1981 | Hansen |
| 4,502,492 | A | 3/1985 | Bornzin |
| 4,762,135 | A | 8/1988 | Van Der Puije |
| 4,827,932 | A | 5/1989 | Ideker |
| 4,938,231 | A | 7/1990 | Milijasevic |
| 5,042,463 | A | 8/1991 | Lekholm |
| 5,344,387 | A | 9/1994 | Lupin |
| 5,454,370 | A | 10/1995 | Avitall |
| 5,649,970 | A | 7/1997 | Loeb |

(Continued)

FOREIGN PATENT DOCUMENTS

| EP | 2286871 A2 | 2/2011 |
| EP | 2298408 A2 | 3/2011 |

(Continued)

OTHER PUBLICATIONS

Ruddy, et al. "Influence of materials and geometry on fields produced by cochlear electrode arrays", Medical & Biological Engineering & Computing, 1995, 793-801, 33.

(Continued)

Primary Examiner — Alyssa M Alter
(74) Attorney, Agent, or Firm — Fabian Vancott; Steven L. Nichols

(57) ABSTRACT

A cochlear lead includes a thermoformed circuit with a substrate with electrodes formed on the substrate and shaped to curve around a longitudinal axis of the cochlear lead. Traces are also formed on the substrate and connected to the electrodes. Intermediate sections between the electrodes may be curved about an axis that is orthogonal to the longitudinal axis.

15 Claims, 18 Drawing Sheets

(56) References Cited

U.S. PATENT DOCUMENTS

| | | | |
|---|---|---|---|
| 6,074,422 A | 6/2000 | Berrang | |
| 6,304,787 B1 | 10/2001 | Kuzma | |
| 6,309,410 B1 | 10/2001 | Kuzma | |
| 6,374,143 B1 * | 4/2002 | Berrang | A61N 1/0541 600/379 |
| 6,546,292 B1 | 4/2003 | Steinhaus | |
| 6,779,257 B2 | 8/2004 | Kiepen | |
| 6,889,094 B1 | 5/2005 | Kuzma | |
| 7,326,649 B2 | 2/2008 | Rodger | |
| 7,706,888 B2 | 4/2010 | Jolly | |
| 7,983,768 B2 | 7/2011 | Dadd | |
| 8,000,798 B2 | 8/2011 | Gantz | |
| 8,014,878 B2 | 9/2011 | Greenberg | |
| 8,126,564 B2 | 2/2012 | Gantz | |
| 8,180,460 B2 | 5/2012 | Neysmith | |
| 8,190,271 B2 | 5/2012 | Overstreet | |
| 8,250,745 B1 | 8/2012 | Orinski | |
| 8,332,052 B1 | 12/2012 | Orinski | |
| 8,880,193 B1 | 11/2014 | Thenuwara | |
| 9,056,196 B2 | 6/2015 | Thenuwara | |
| 9,211,403 B2 | 12/2015 | Tortonese | |
| 2002/0019669 A1 | 2/2002 | Berrang | |
| 2005/0038489 A1 | 2/2005 | Grill | |
| 2005/0256561 A1 | 11/2005 | Gantz | |
| 2006/0074460 A1 | 4/2006 | Maghribi | |
| 2006/0116743 A1 | 6/2006 | Gibson | |
| 2006/0247754 A1 | 11/2006 | Greenberg | |
| 2006/0259112 A1 | 11/2006 | Greenberg | |
| 2007/0112402 A1 | 5/2007 | Grill | |
| 2007/0179566 A1 | 8/2007 | Gantz | |
| 2007/0203557 A1 | 8/2007 | Gantz | |
| 2007/0251082 A1 | 11/2007 | Milojevic | |
| 2007/0293749 A1 | 12/2007 | Zhou | |
| 2008/0015669 A1 | 1/2008 | Jolly | |
| 2008/0019518 A1 | 1/2008 | Mito | |
| 2008/0057179 A1 | 3/2008 | Greenberg | |
| 2008/0064946 A1 | 3/2008 | Greenberg | |
| 2008/0195178 A1 | 8/2008 | Kuzma | |
| 2008/0234793 A1 | 9/2008 | Gibson | |
| 2008/0288036 A1 | 11/2008 | Greenberg | |
| 2008/0288037 A1 | 11/2008 | Neysmith | |
| 2008/0312717 A1 | 12/2008 | Gantz | |
| 2009/0030483 A1 | 1/2009 | Risi | |
| 2009/0143848 A1 | 6/2009 | Greenberg | |
| 2009/0306745 A1 | 12/2009 | Parker | |
| 2010/0106134 A1 | 4/2010 | Jolly | |
| 2010/0168830 A1 | 7/2010 | Hung | |
| 2010/0204768 A1 | 8/2010 | Jolly | |
| 2011/0202120 A1 | 8/2011 | Ball | |
| 2011/0264168 A1 | 10/2011 | Dadd | |
| 2011/0301665 A1 | 12/2011 | Mercanzini | |
| 2011/0319907 A1 | 12/2011 | Gallegos | |
| 2012/0004715 A1 * | 1/2012 | Ramachandran | A61N 1/0541 607/137 |
| 2012/0158113 A1 | 6/2012 | Jolly | |
| 2012/0192416 A1 | 8/2012 | Neysmith | |
| 2014/0303703 A1 | 10/2014 | Mercanzini | |
| 2014/0336739 A1 | 11/2014 | Lotfi | |
| 2015/0267314 A1 | 9/2015 | Thenuwara | |
| 2015/0320550 A1 | 11/2015 | Downing | |

FOREIGN PATENT DOCUMENTS

| | | |
|---|---|---|
| WO | 0112115 | 2/2001 |
| WO | 2008011721 A9 | 1/2008 |
| WO | 2009062114 A2 | 5/2009 |
| WO | 2009121110 | 10/2009 |
| WO | 2010055421 | 5/2010 |
| WO | 2011075480 | 6/2011 |
| WO | 2012003295 A1 | 1/2012 |
| WO | 2012003297 A1 | 1/2012 |
| WO | 2012034162 A2 | 3/2012 |
| WO | 2012154256 | 11/2012 |
| WO | 20140105059 A1 | 12/2012 |
| WO | 2013048396 A1 | 4/2013 |
| WO | 2013103489 | 7/2013 |
| WO | 2015023280 | 2/2015 |
| WO | 2015030734 | 3/2015 |

OTHER PUBLICATIONS

Wei, et al.; "Analysis of high-perimeter planar electrodes for efficient neural stimulation"; Frontiers in Neuroengineering; Nov. 2009; vol. 2.

Wei, Xuefeng Frank; "Analysis and Design of Electrodes for Deep Brain Stimulation"; Doctoral Thesis; Dept. of Biomedical Engineering; Duke University; 2009.

* cited by examiner

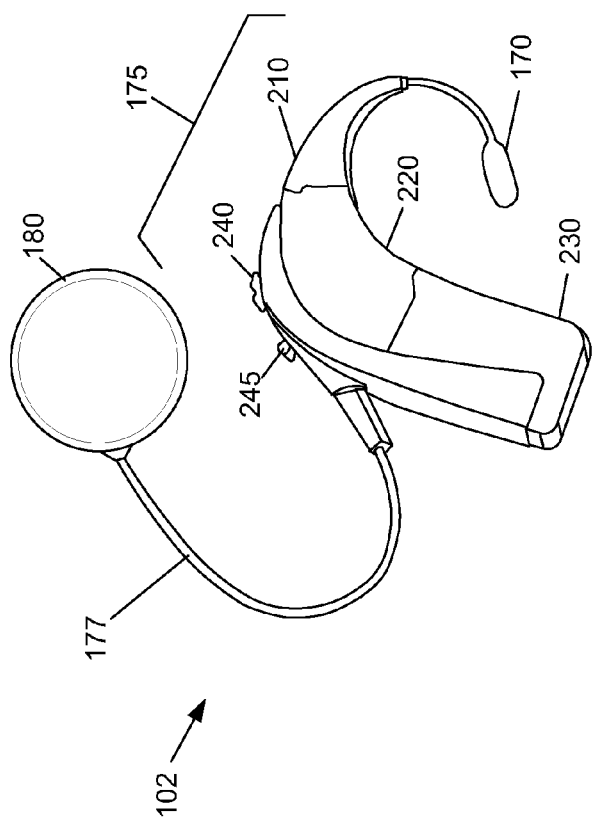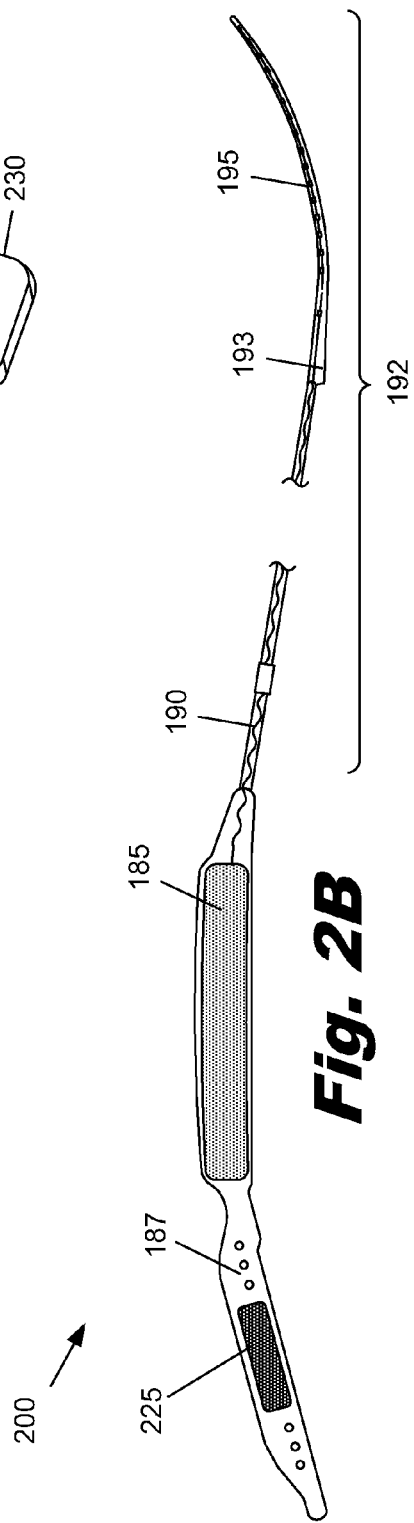

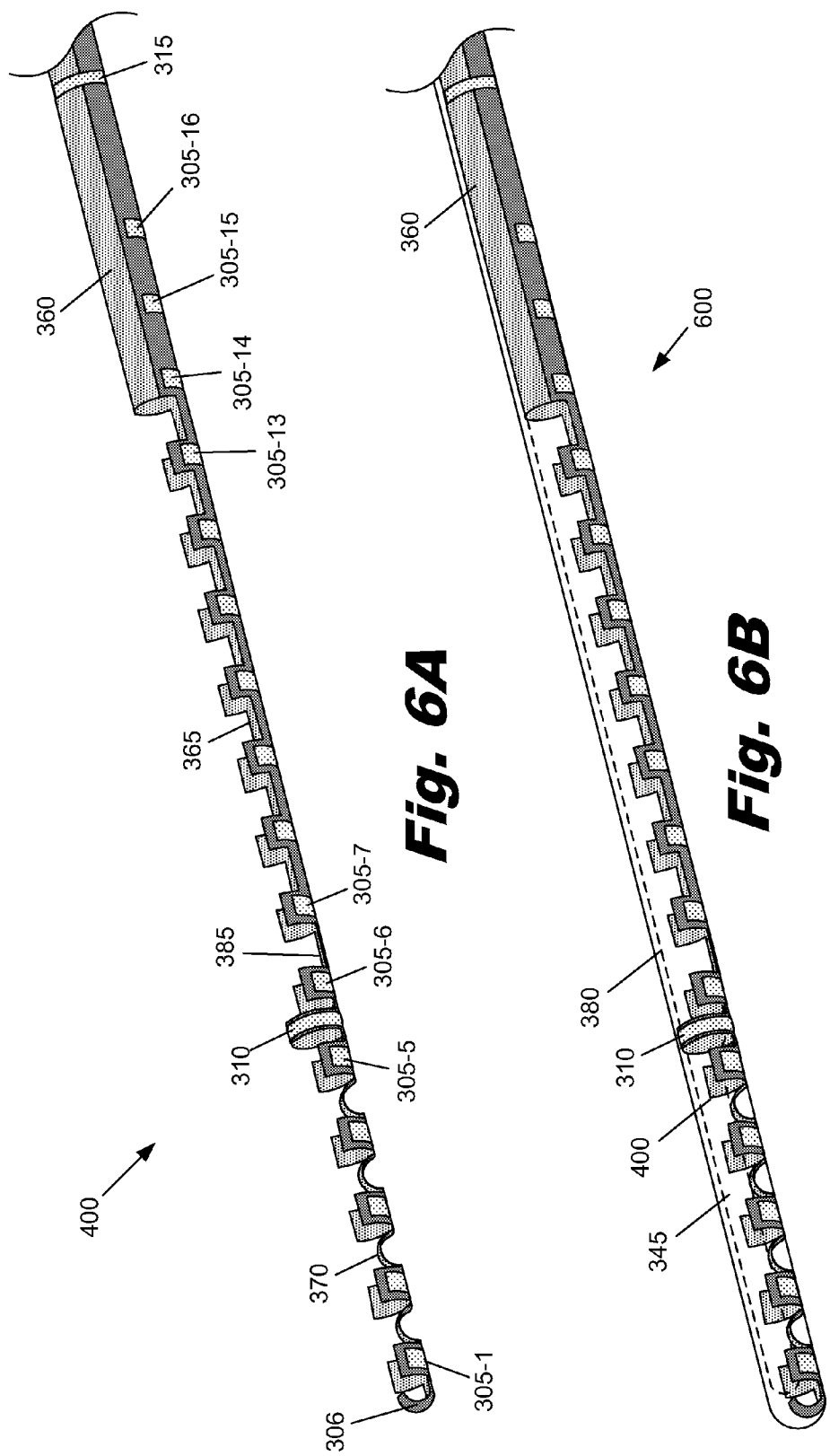

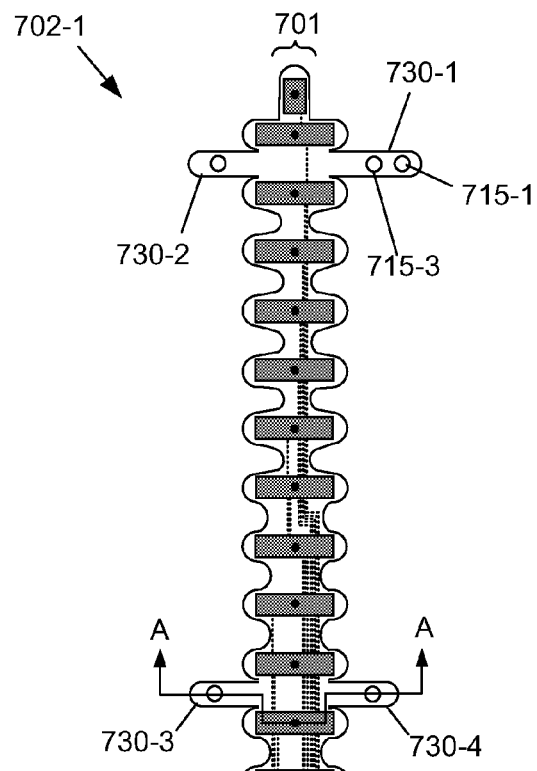
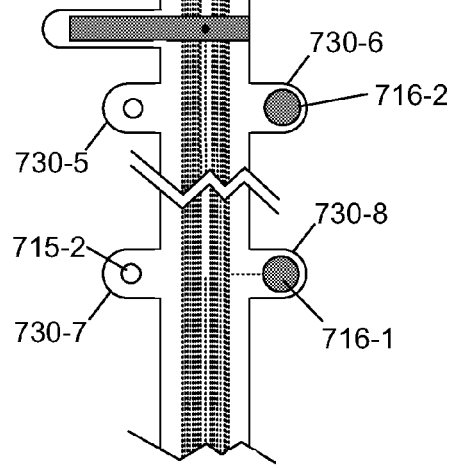
Fig 7C

780

```
┌─────────────────────────────────────┐
│ Forming a circuit on a circuit      │
│ substrate, the circuit substrate    │
│ comprising a thermoplastic          │
│                                     │
│              785                    │
└─────────────────────────────────────┘
                 │
                 ▼
┌─────────────────────────────────────┐
│ Cutting the circuit substrate to    │
│ form a first flag extension having  │
│ an aperture passing through the     │
│ circuit substrate                   │
│              790                    │
└─────────────────────────────────────┘
                 │
                 ▼
┌─────────────────────────────────────┐
│ Aligning the circuit substrate in a │
│ thermoforming mold by inserting a   │
│ first alignment feature into        │
│ the aperture                        │
│              795                    │
└─────────────────────────────────────┘
                 │
                 ▼
┌─────────────────────────────────────┐
│ Thermoforming the circuit substrate │
│ into a predetermined geometry.      │
│                                     │
│              797                    │
└─────────────────────────────────────┘
```

*Fig. 7F*

Section D-D

THERMOFORMED ELECTRODE ARRAYS

BACKGROUND

Neurostimulating devices stimulate nerves by applying an electrical current. Such devices often include a biocompatible wire construct that carries current from a pulse generator or radio frequency link to the stimulation site. These wire constructs can include multiple small diameter wires and are typically constructed manually. Manually handling and connecting the wires is expensive, time consuming and can result in significant variation in the spacing and organization of the wires that make up the wire construct.

BRIEF DESCRIPTION OF THE DRAWINGS

The accompanying drawings illustrate various examples of the principles described herein and are a part of the specification. The illustrated examples are merely examples and do not limit the scope of the claims.

FIGS. 2A and 2B show the external and internal portions of a cochlear implant system, respectively, according to one example of principles described herein.

FIG. 6A is a perspective view of a thermoformed circuit, according to one example of principles described herein.

FIG. 6B is a perspective view of a thermoformed circuit encapsulated in silicone with a lumen passing down the longitudinal axis of the thermoformed circuit, according to one example of principles described herein.

FIGS. 7A-7F describe a thermoformed circuit with flag extensions according to one example of principles described herein.

Throughout the drawings, identical reference numbers designate similar, but not necessarily identical, elements.

DETAILED DESCRIPTION

As discussed above, neurostimulating devices often include a biocompatible wire construct that carries current to the stimulation site. These wire constructs can include multiple small diameter wires and are typically constructed manually. Manually handling the wires is laborious and requires skilled technicians. This manual assembly process can result in significant variation in the spacing and organization of the wires that make up the wire construct. This can lead to undesired variations in the geometry and properties within and between wire constructs. Additionally, the manual manufacturing can be expensive because it is a low yield and a low throughput process.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example" or similar language means that a particular feature, structure, or characteristic described in connection with the example is included in at least that one example, but not necessarily in other examples. Features shown and/or described in connection with one figure may be combined with features shown and/or described in connection with other figures.

Figure 1:
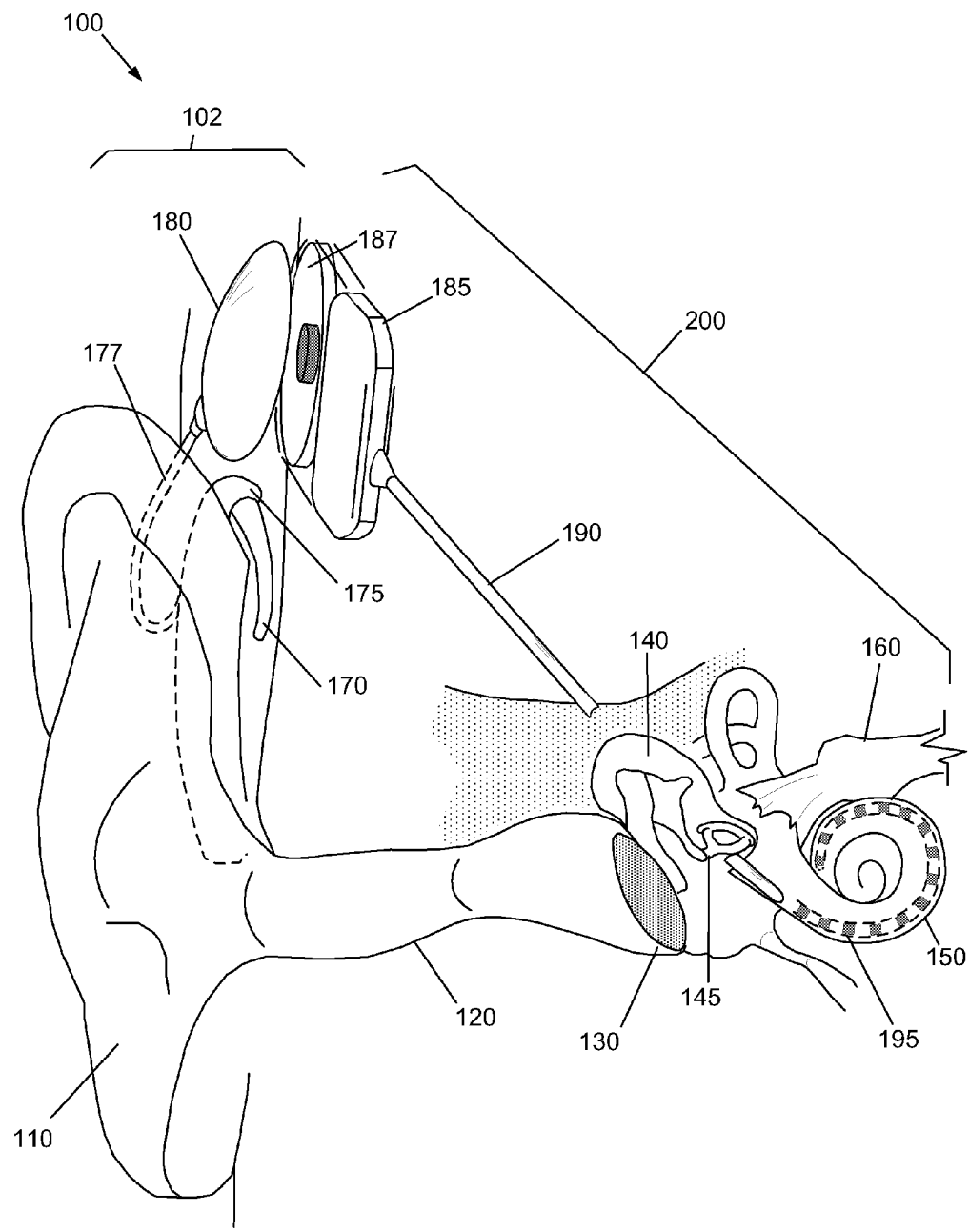
FIG. 1 shows a cochlear implant system in use by a patient, according to one example of principles described herein.

FIG. 1 is a diagram showing one illustrative example of a neurostimulating cochlear implant system (100) that includes an internal implanted portion (200) and an external portion (102). In a functioning human ear, sound enters the external ear (110) and passes through the ear canal (120) to the ear drum (130). A series of three small bones (145) in the middle ear (140) amplify the motion of the ear drum and transmit the amplified signals to the cochlea (150). Fluid inside the cochlea (150) moves in response to the amplified signals. Hair cells in the cochlea (150) convert the motion of the fluid into nerve impulses that travel through the auditory nerve (160) to the brain.

The cochlear implant system (100) provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

The external portion (102) of the cochlear implant system (100) can include a Behind-The-Ear (BTE) unit (175), which contains the sound processor and has a microphone (170), a cable (177), and a transmitter (180). The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the BTE unit (175) and transmits them to the implanted antenna assembly (187) by electromagnetic transmission. FIG. 2A shows the external portion (102) of the cochlear implant system (100, FIG. 1), including the BTE unit (175), battery (230), processor (220), ear hook (210), and microphone (170). A number of controls (240, 245) are located on the processor (220). These controls may include an on/off switch (245) and volume switch (240). The cable (177) connects the processor (220) to the transmitter (180).

FIG. 1 also shows the internal implanted portion (200) of the cochlear implant system that includes an electrode array (195) that is surgically placed within the patient's cochlea (150). Unlike hearing aids, the cochlear implant system (100) does not amplify sound, but works by directly stimulating any functioning auditory nerve cells inside the cochlea (150) with electrical impulses representing the ambient acoustic sound. This bypasses the defective cochlear hair cells that normally transduce acoustic energy into electrical energy.

The implanted portion (200) of the cochlear implant system is shown in FIG. 1 in its implanted configuration and in FIG. 2B before implantation. The implanted portion (200) of the cochlear implant system (100) includes an internal processor (185), an antenna assembly (187), and an implantable lead (192). The implantable lead (192) includes a lead body (190) and an electrode array (195). The internal processor (185) and antenna assembly (187) are secured beneath the user's skin, typically above and behind the external ear (110). The antenna assembly (187) receives signals and power from the transmitter (180). The internal processor (185) receives these signals and operates on the signals to generate modified signals. These modified signals are then sent through the lead body (190) to the electrode array (195), which is at the distal portion of the implantable lead (192) and is implanted within the cochlea (150). The electrode array uses the modified signals to provide electrical stimulation to the auditory nerve (160).

FIG. 2B is a side view of the implanted portion (200) of a cochlear implant system (100, FIG. 1). The implanted portion (200) includes the antenna assembly (187) and the processor (185). In this example, the antenna assembly (187) is external from the processor (185). A magnet (225) is disposed in the center of the antenna assembly (187). The magnet (225) removably secures the transmitter (180, FIG. 1) over the antenna assembly (187). The antenna assembly (187) is connected to the processor (185). The implantable lead (192) is connected to the opposite side of the processor (185). The implantable lead (192) includes the electrode array (195) and the lead body (190). The electrode array (195) is inserted into one of the cochlear ducts, such as the scale tympani.

As used in the specification and appended claims, the terms "proximal" and "distal" refer to the relationship of the device with respect to a surgeon inserting the device into a patient. A proximal element is closer to the surgeon and a distal element is farther away from the surgeon. In FIG. 2B, the surgeon grasps a protrusion (193) at the junction of the lead body (190) and the electrode array (195) and inserts the tip of the electrode array (195) into the cochlea (150). Consequently, the tip of the electrode array (195) is in a more distal location than the protrusion (193).

Figure 3A:
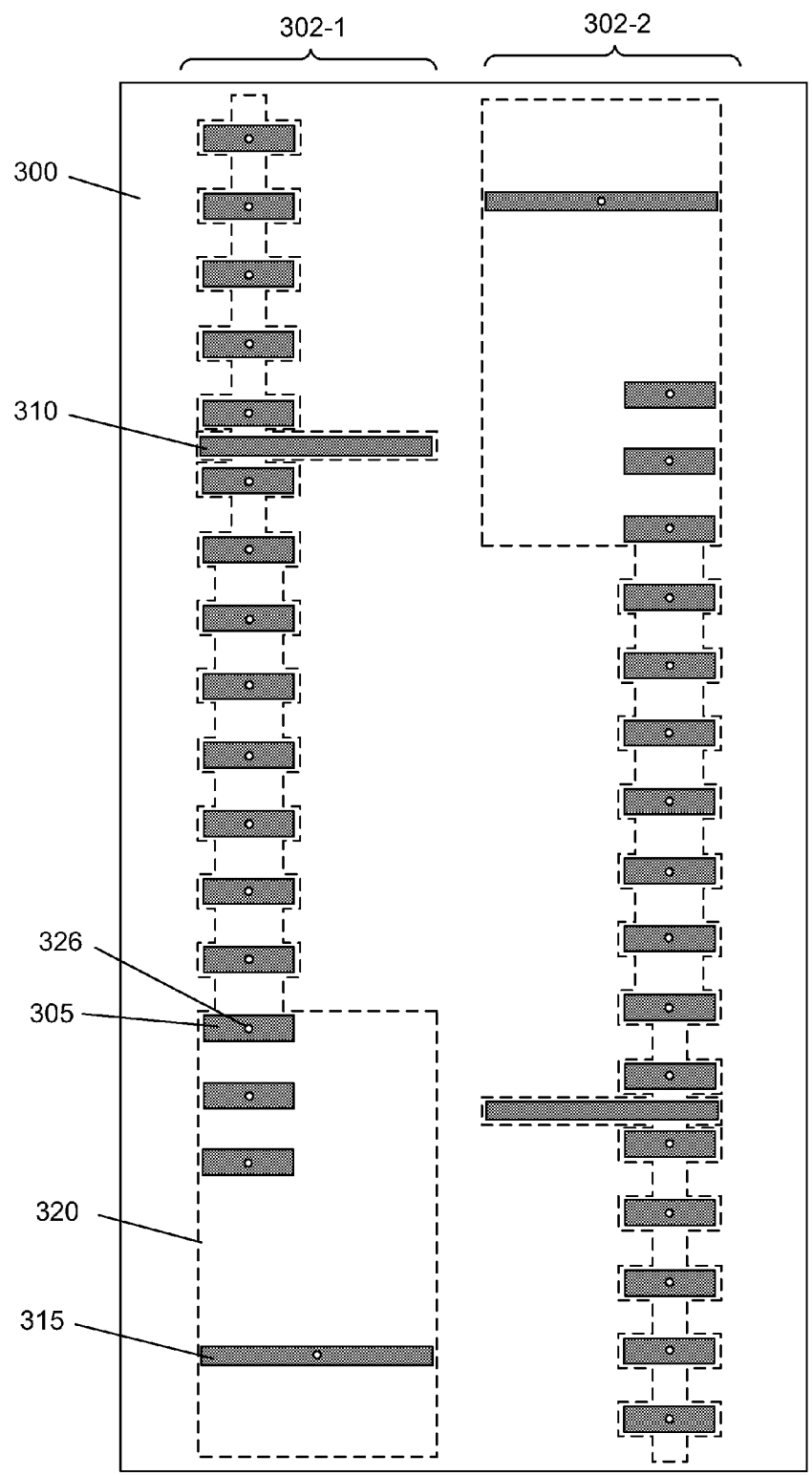
FIG. 3A is a plane/planar view of a substrate with electrodes formed thereon, according to one example of principles described herein.
Figure 3B:
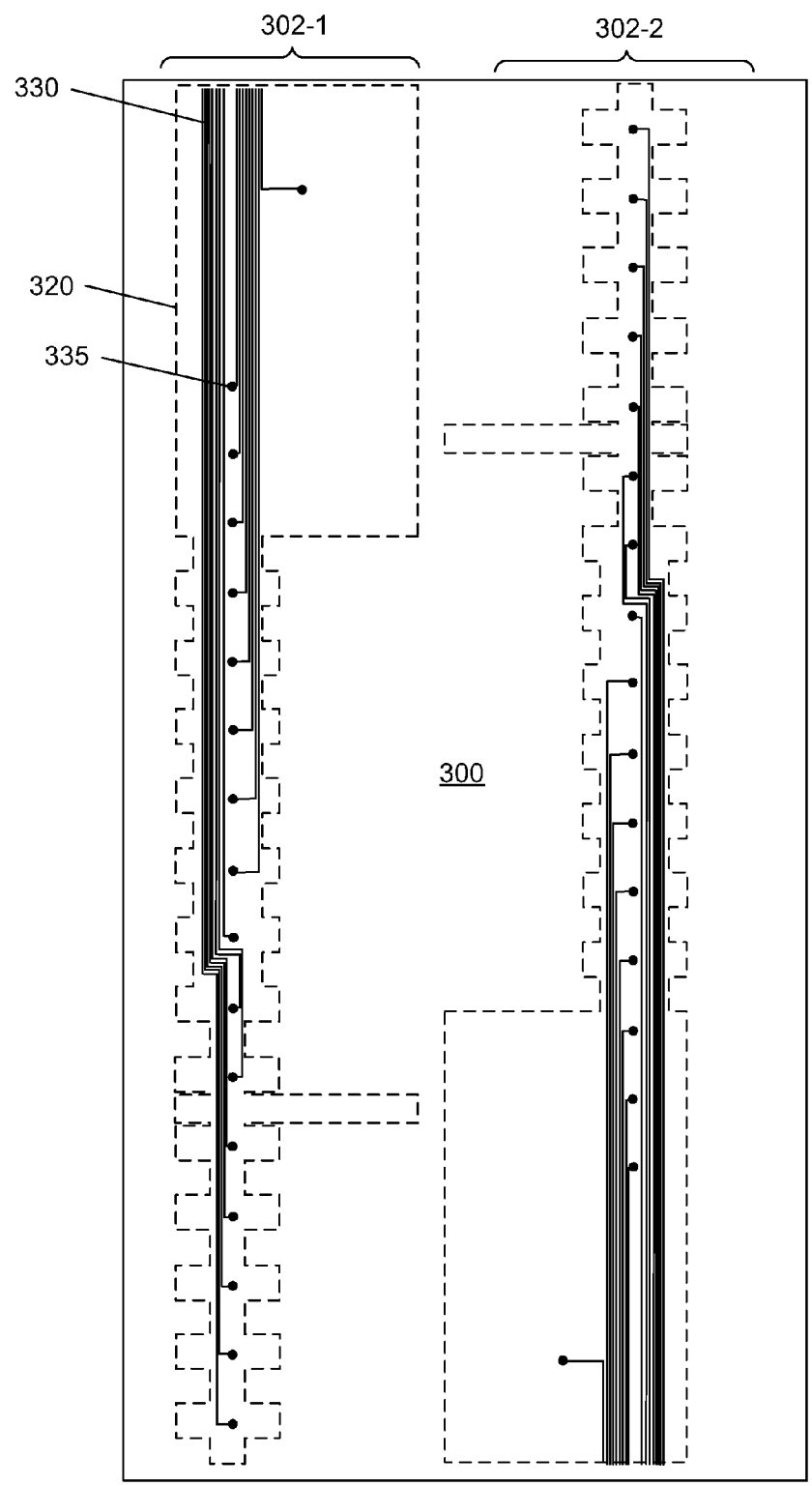
FIG. 3B is a plane/planar view of a substrate of FIG. 3A with traces and vias formed on the substrate, according to one example of principles described herein.
Figure 3C:
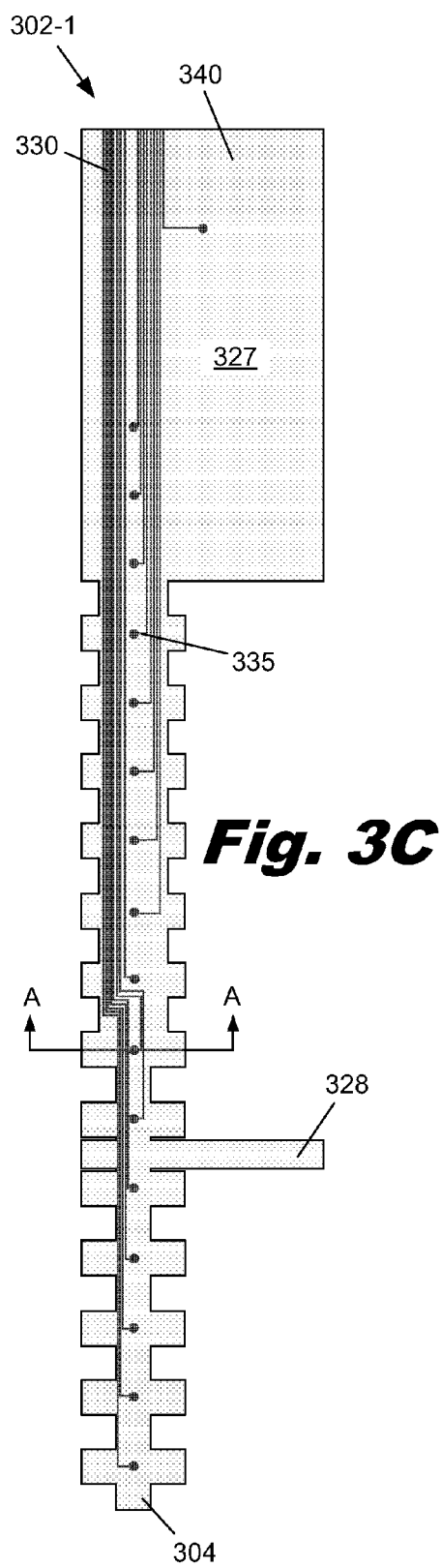
FIGS. 3C and 3D show a back view and a front view of an electrode array formed on the substrate, respectively, according to one example of principles described herein.
Figure 3D:
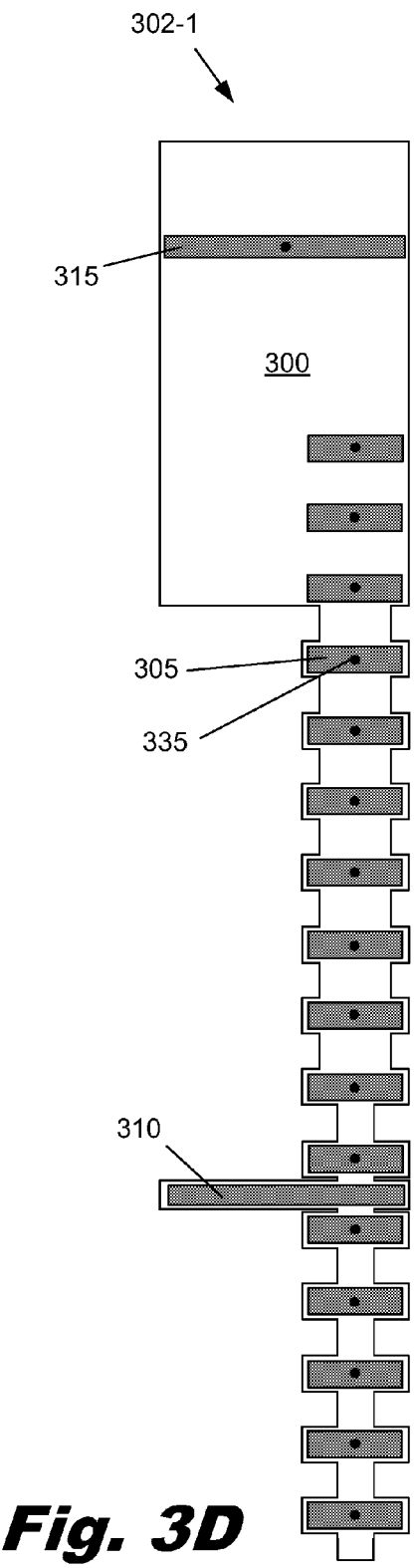
Figure 4A:
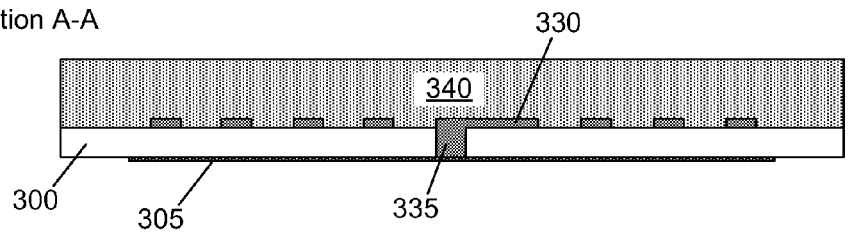
FIG. 4A is a cross sectional diagram of a cochlear electrode array formed on a substrate with a thermoplastic layer adhered to the substrate, according to one example of principles described herein.
Figure 4B:
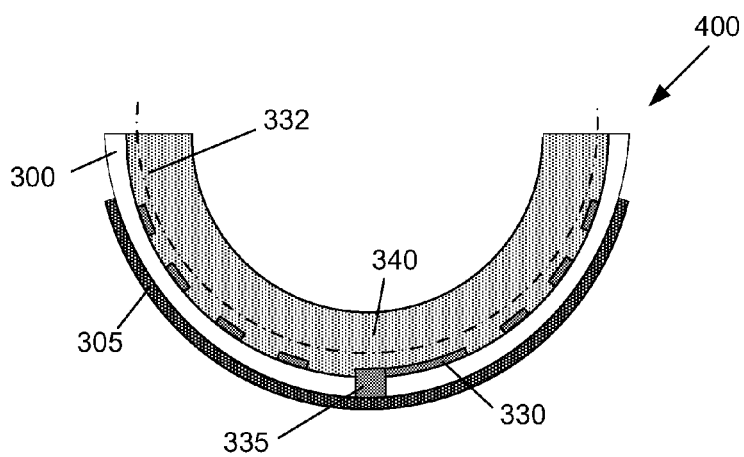
FIG. 4B is a cross sectional diagram of a cochlear electrode array with a thermoplastic layer that has been thermoformed into a desired shape, according to one example of principles described herein.

FIGS. 3A-3B show formation of electrode circuits on a substrate. These electrode circuits are cut from the substrate (as shown in FIGS. 3C-3D) and thermoformed into a desired shape (as shown in FIG. 4A-4B). Encapsulation of a thermoformed circuit in a flexible body (FIG. 4C, 6A) produces the electrode array (195, FIG. 2B, 6B). These implementations described in these figures are only illustrative examples. A variety of other approaches could be used to implement the principles described. Each of the figures is described in more detail below.

FIG. 3A shows a substrate (300) upon which two electrode circuits (302-1, 302-2) will be formed. The substrate (300) may be any of a number of materials, including a flexible substrate formed from polymer material. For example, the substrate (300) may be formed from a thermoplastic material. A number of electrodes (305, 315) are formed on an upper face of the substrate (300). These electrodes may include stimulating electrodes (305), and ring electrodes (315). Any of the electrodes may be electrically active and the electrodes may be formed in any desired shape or configuration. In this example, the stimulating and ring electrodes (305, 315) have a through hole (326) that passes through the electrode and the substrate. These through holes (326) will later be used to form vias that connect traces that will be formed on the opposite side of the substrate (300) to the stimulating and ring electrodes (305, 315).

Markers (310) may also be formed on the substrate (300). For example, the markers (310) may be formed using the same processes and materials used to form electrodes. However, a marker is not electrically active and is not connected to a trace. In other examples, the markers (310) may be formed using different materials and/or processes than those used to form the electrodes. For example, the markers (310) may be selected from materials that exhibit different visual or radio properties than the electrode. The markers may be exposed or may be encapsulated within the flexible body.

The dashed outlines (320) show where the electrode circuits (302-1, 302-2) will subsequently be cut out of the substrate (300). In the example shown in FIG. 3A, there are two electrode circuits (302-1, 302-2) nested together. The nesting of these electrode circuits together allows for multiple circuits to be formed at the same time. This can increase efficiency in the production of the electrode circuits by reducing handling and fixturing times. The combination of two or more electrode circuits that are formed in a single substrate is called a "tray" of electrode circuits. In the example shown in FIGS. 3A and 3B, only two electrode circuits are in the tray. However, any number of electrode circuits may be included in the tray and formed simultaneously during the processing steps. There are a variety of ways to form the electrodes on the substrate, including lithographic, printing, deposition, plating techniques, etching and other suitable processes.

In FIG. 3B, the substrate (300) has been flipped around a horizontal axis to show the opposite side of the substrate (300). In this step of the manufacturing process, a number of traces (330) are formed. During the formation of the traces (or during formation of the electrodes) the through holes (326) are filled to form vias (335). As discussed above, these vias connect traces (330) on the back side of the substrate to the electrodes on the front side of the substrate. The electrodes, traces, (330) and vias (335) can be formed from any appropriate material using any appropriate process. For example, the material may be a chemically inert conductive metal such as gold, platinum, iridium or alloys thereof. The traces, electrodes and vias can be formed using a number of processes, including printing processes, lithography, deposition and etching, etc. In some examples, the conductive elements on the substrate may be formed using a combination of processes. For example, the traces may be initially formed using a lithographic process and then thickened using electrochemical plating processes. After the desired planar processing has been performed, the individual electrode circuits (302-1, 302-2) may be cut from the substrate along the dashed line (320).

FIGS. 3C and 3D show the back and front sides of the circuit (302-1) after it has been cut out of the substrate (300). The circuit (302-1) can be cut from the substrate (300) using a variety of techniques including laser cutting. For example, femtosecond laser cutting may be used for precisely cutting along the desired lines and to avoid damaging surrounding portions of the substrate. The back of the circuit (302-1) is shown in FIG. 3C and the front of the circuit (302-1) is shown in FIG. 3D. In this example, a thermoplastic layer (340) has been connected to the back of the substrate before the laser cutting step so that the traces (330) are sandwiched between the substrate (300, FIG. 3D) and the thermoplastic layer (340). This covers the traces and protects them from damage. In FIG. 3C, the thermoplastic layer (340) has been illustrated as being partially transparent so that the traces (330) can be seen through it. However, the thermoplastic layer (340) may or may not exhibit transparency.

The cutout shape of the circuit (302-1) includes a number of extensions such as a basal extension (327) and a ring electrode extension (328). There is also an extension (304) protruding out of the distal end of the circuit. FIG. 3D shows the front side of the circuit (302-1). The front side includes the electrodes (305, 315) and vias (335) connecting the traces (330, FIG. 3C) to the electrodes (305, 310). The marker 315 may be used for a variety of purposes including as a marker indicating a depth of insertion. For example, the marker 315 may indicate a maximum insertion depth just before it passes into the cochlea.

Figure 4C:
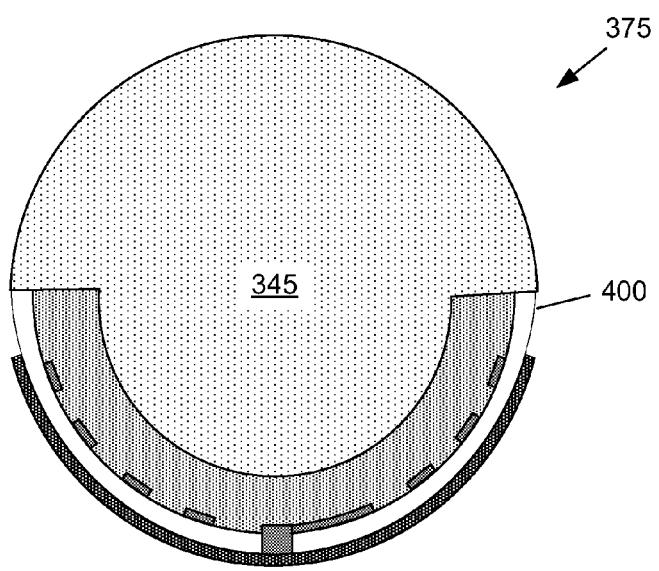
FIG. 4C is a cross sectional view of a thermoformed cochlear electrode array that includes overmolding/encapsulation with silicone, according to one example of principles described herein.

FIGS. 4A-4C show a cross section of the circuit taken along section line A-A as shown in FIG. 3C. FIG. 4A shows the cross section of the circuit (302-1, FIG. 3C) including the substrate (300) with the electrode (305) formed on an exterior surface of the substrate (300), traces (330) formed on the opposite (interior) side of the substrate (300) and vias (335) selectively connecting the traces (330) to the electrode (305). The thermoplastic layer (340) is deposited on the interior of the substrate so that the traces are sandwiched between the substrate (300) and the thermoplastic layer (340).

Thermoplastic is a polymer that becomes pliable or moldable above a certain temperature ("glass transition temperature") and then returns to its solid (less pliable, resilient) state upon cooling. The thermoplastic typically is formed from polymer molecules with a high molecular weight. The bonds in the thermoplastic are intermolecular bonds rather than stronger covalent atomic bonds. These properties allow the thermoplastics to be remolded multiple times because the intermolecular bonds spontaneously reform upon cooling. Thermoplastics differ from thermosetting polymers that form irreversible chemical bonds during the curing process. Examples of thermoplastics include acrylics, vinyls, polyacrylates, polyamides, polypropylene, polyurethanes, polyethanes, polybutylenes, polyesters, polyethylene, and other materials. When the temperature of a thermoplastic is above a glass transition temperature but below the melt temperature, the properties of the thermoplastics change drastically without the thermoplastic becoming liquid. Within this temperature range, the thermoplastic becomes rubbery and readily moldable. Upon cooling, the thermoplastic will retain the shape that it has been formed into. In general, the thermoplastic used is biocompatible. Tests for biocompatibility include evaluation of the chemical stability of the thermoplastic in a biological environment and reaction of the biological environment to the implanted thermoplastic. There are several thermoplastics that may be suitable for permanent implants, including polypropylene and polyethylene.

The thermoplastic layer may be bonded to the flexible substrate using any of a number of techniques, including adhesive, thermobonding, ultrasonic welding, or other suitable techniques. In general, thermobonding refers to the application of heat and pressure to join the surface of the substrate with the thermoplastic layer.

The above discussion is only one example of principles described herein. A variety of other structures and techniques could also be used to implement the principles. Other configurations, materials, and geometries could be used. For example, the substrate (330) itself may be thermoplastic and may be thermoformed into a predetermined shape. In this case the additional thermoplastic layer (340) may not be necessary. In other examples, the substrate (300) could be a thermoplastic material that is folded over to form a multi-layer circuit. Thus, the folded substrate (330) serves as both the substrate (300) and the thermoplastic layer (340). This may allow for additional traces (330), larger cross sectional traces, and potentially reduce the number of manufacturing steps.

FIG. 4B shows the circuit (302-1, FIG. 3C) after it has been thermoformed to produce a thermoformed circuit (400) with a predetermined shape. The thermoforming process includes heating the circuit and forming the circuit into the desired shape. In this example, the predetermined shape along the cross section A-A is a circular arc with the electrode (305) on the exterior of the arc and the thermoformed thermoplastic layer (340) on the interior of the arc. The traces (330) are sandwiched between the substrate (300) and the thermoplastic layer (340) near the neutral bending axis (332) as shown by a dash-dot line. This may minimize bending forces on the traces (330). The electrode (305) may be relatively thin prior to thermoforming so that it is more flexible. After thermoforming, the electrode (305) may be thickened to improve its electrical characteristics. For example, electroplating or other processes may be used to thicken the electrode. In other examples, the electrode may be entirely formed prior to thermoforming.

FIG. 4C shows the thermoformed circuit (400) attached to a flexible body (345) to form a cochlear electrode array (375). The flexible body (345) may be formed from a variety of biocompatible flexible materials including silicone. In one example, the flexible body (345) may be formed around/into the thermoformed circuit (400) using insert liquid injection molding. For example, the circuit may be placed and held in a predetermined position within a liquid injection mold, with the electrodes against a wall of the mold. Liquid silicone may then be injected into the liquid injection mold. The liquid silicone bonds with the thermoformed circuit. When the silicone has cured, the cochlear electrode array (375) is removed from the mold. The cochlear electrode array (375) may have a number of additional features, including a lumen, flag extensions, and additional layers.

Figure 5:
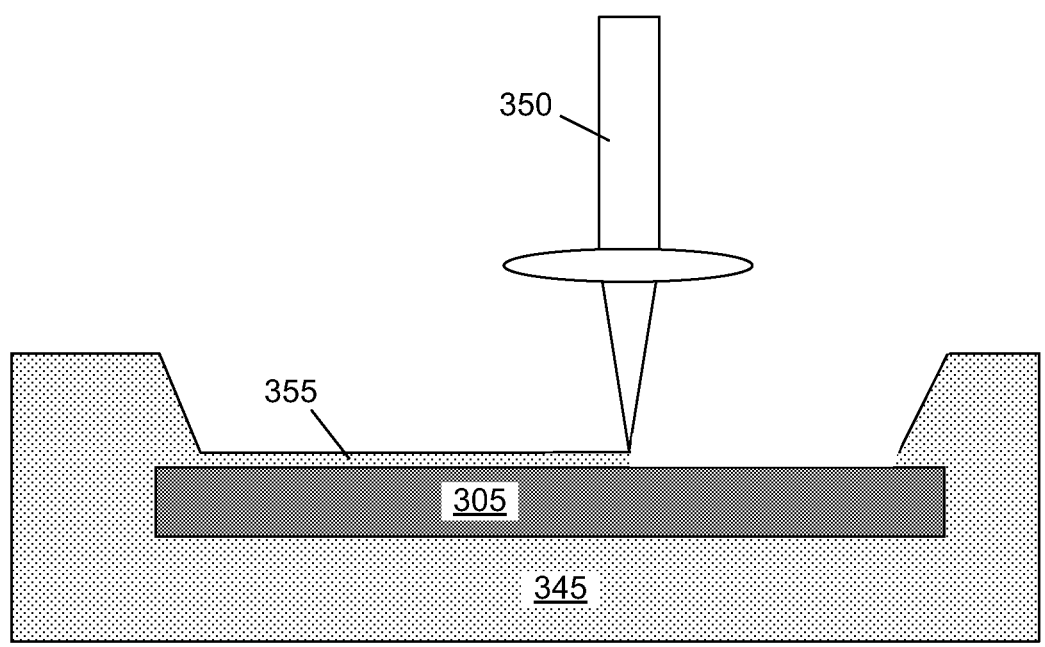
FIG. 5 shows a side view of a laser removing silicone flash overlying an electrode, according to one example of principles described herein.

However, in some implementations, a thin layer of silicone ("flash") may be intentionally or unintentionally formed on all or part of the electrode surface area. This can be undesirable because the flash insulates the surface of the electrode and increases the impedance between the surrounding tissues and the electrode. FIG. 5 shows flash (355) covering the surface of an electrode (305). A laser (350) can be used to remove the flash (355). In some examples, the laser operation may be used to simultaneously texture the surface of the electrode (305). For example, an excimer laser can be used to create a surface on a platinum electrode that increases the surface area of the electrode while creating a texture that resists biofilm deposition. A predetermined surface texture can be produced by controlling the laser operation parameters such as pulse length, power, scanning speed, focus, and other parameters.

FIG. 6A shows one example of a thermoformed circuit (400). In this example, the basal extension (327, FIG. 3C) has been rolled into a tube (360) with the ring electrode (315) extending around the exterior of the tube (360). The tube (360) may form part of a lumen that extends along the length of the electrode array. The adjacent edges of the tube may or may not be bonded together at this point. In one implementation, the edges of the thermoformed plastic (or other layer) may be connected during the thermoforming process. For example, thermoformed plastic may be adhered together by application of heat, pressure, chemical adhesives, or other technique. In other examples, the edges of the tube may not be joined during thermoforming but may be joined together during liquid injection molding by the flexible encapsulant. In some examples, the tube may form a portion of a lumen that passes through the length of the cochlear electrode array.

For convenience, the array of stimulating electrodes with similar size and shape have been numbered in FIG. 6A, with the most distal electrode (305-1) designated as electrode number 1 and the most proximal electrode (305-16) labeled as electrode number 16. In this example, the sixteen stimulating electrodes (305) have similar size and shape throughout the electrode array and have been formed into a convex shape that conforms to and defines the exterior shape of the cochlear electrode array (375, FIG. 4C).

The dimensions and shape of the thermoformed circuit are configured to provide varying levels of flexibility along the length of the electrode array. The proximal portions of the electrode array are stiffer and the distal portions of the electrode array are more flexible. This provides a number of benefits. The surgeon, using an appropriate surgical implement, typically grasps the proximal end of the electrode array. By making the proximal end of the electrode array relatively stiff, the surgeon has more control and can more precisely and accurately maneuver the electrode array during the implantation process. Further, the proximal portion of the electrode array resides in the relatively straight basal region of the cochlea. As the electrode array is inserted into the cochlea, the distal end of the electrode array bends into an ascending spiral to follow the curves of the cochlear duct. The flexibility of the distal portions of the electrode array allow for this bending to occur with minimal application of force. The marker (310) may serve as a reference for the surgeon during the insertion process.

In this implementation, the tube (360) at the proximal end of the electrode array is relatively stiff and has similar stiffness in all directions. This provides a stable and relatively stiff portion of the electrode array for the surgeon to grasp and manipulate. The ring electrode (315) and the most proximal three stimulating electrodes (305-14, 305-15, 305-16) are disposed on the outer surface of the tube (360). The remaining active electrodes in this implementation are joined by intermediate sections that have different widths and geometries. These intermediate sections include curved proximal intermediate sections (365) that connect electrodes 305-7 through 305-14, a flat intermediate section (385) that connects the sixth electrode (305-6) to the seventh electrode (305-7), and arched intermediate sections (370) that join electrodes 305-1 through 305-5. The proximal intermediate sections (365) curve about a longitudinal axis of the cochlear lead and are relatively stiff. The flat intermediate section (385) is less stiff, and the distal arched intermediate sections (370) curve about a orthogonal axis and are significantly more flexible that the other sections. The curvature of the intermediate sections can provide different amounts of flexibility in various directions. For example, the arched intermediate sections (370) are specifically designed to provide flexibility curvatures that occur when the electrode array curls about the modiolus of the cochlea. However, the stiffness in other directions may be significantly greater.

The thermoformed end feature (306) has been created from the end extension (304). The thermoformed end feature (306) may provide a number of functions. In this example, the end feature (306) may curl upward and back toward the interior and/or proximal end of the electrode array. In implementations where a lumen extends along the length of the electrode array, the end feature could act as a stop that prevents a stylet inserted in the lumen from puncturing the end of the flexible body (345, FIG. 4C). Additionally or alternatively, the end feature (306) may include an electrode or sensor. The electrode could be used to stimulate neurons that are beyond the end of the electrode array. If a sensor is incorporated into the end feature, the sensor could be used to detect proximity or contact with the cochlear wall. Illustrative principles and examples of sensors and electrodes that could be used in conjunction with the end feature (306) are described in International App. No. PCT/US2012/72138, entitled "Tip Elements for Cochlear Implants," which published as International Pat. Pub. No. WO2014105059, and U.S. application Ser. No. 12/915,375, entitled "Steerable Stylet," which issued as U.S. Pat. No. 9,211,403, which are incorporated herein by reference in their entireties.

FIG. 6B shows a cochlear electrode array (600) that includes the thermoformed circuit (400, FIG. 6A) encapsulated in a silicone flexible body (345). In the example, the flexible body (345) encapsulates the thermoformed circuit (400) except for the electrode surfaces. A lumen (380, shown by the dashed outline) is formed in the silicone flexible body (345). In this example, the lumen (380) passes through the center of the tube (360) and down the center of the electrodes. The lumen (380) ends at the distal tip of the electrode array (600). The diameter of the lumen (380) may change along the length of the electrode array (600). In this example, the lumen (380) has a smaller diameter in the distal portion of the electrode array (600). To insert the cochlear electrode array (600) into a patient's cochlea (150, FIG. 1) during the surgical procedure, the surgeon inserts a stylet into the lumen (380). The stylet may be attached to, or grasped by a surgical insertion tool. The stylet provides additional stiffness to the electrode array (600) and better control over the electrode array (600) during the surgical insertion.

The marker (310) is formed by thermoforming a strip of the circuit into a circle and joining the ends of a strip. In this example, the marker (310) is used to indicate when the surgeon should begin to advance the cochlear electrode array (600) off the stylet that has been inserted into the lumen (380). In general, the structure of a cochlear duct includes a relatively straight basal portion and then an ascending spiral shape. When the marker (310) is aligned with a cochleostomy in the cochlea, the tip of the electrode array is near the portion of the cochlear duct that begins to turn into the circular ascending spiral. The surgeon then begins to advance the cochlear electrode array (600) off the stylet, typically by holding the stylet stationary and pushing the electrode array deeper into the cochlea. Thus, the marker (310) provides a visual reference to the surgeon to indicate when the electrode array should begin to be advanced off the stylet. This prevents the stylet from entering the curved portion of the cochlea. In alternative implementations, the lumen may not extend down the full length of the electrode array and the second electrode may be absent or positioned in a different location.

FIGS. 7A-7F describe an illustrative embodiment that includes a thermoformed substrate with flag extensions. The flag extensions include through holes (apertures) that can be used for alignment during the thermoforming process. The flag extensions may also serve a variety of other purposes.

Figure 7A:
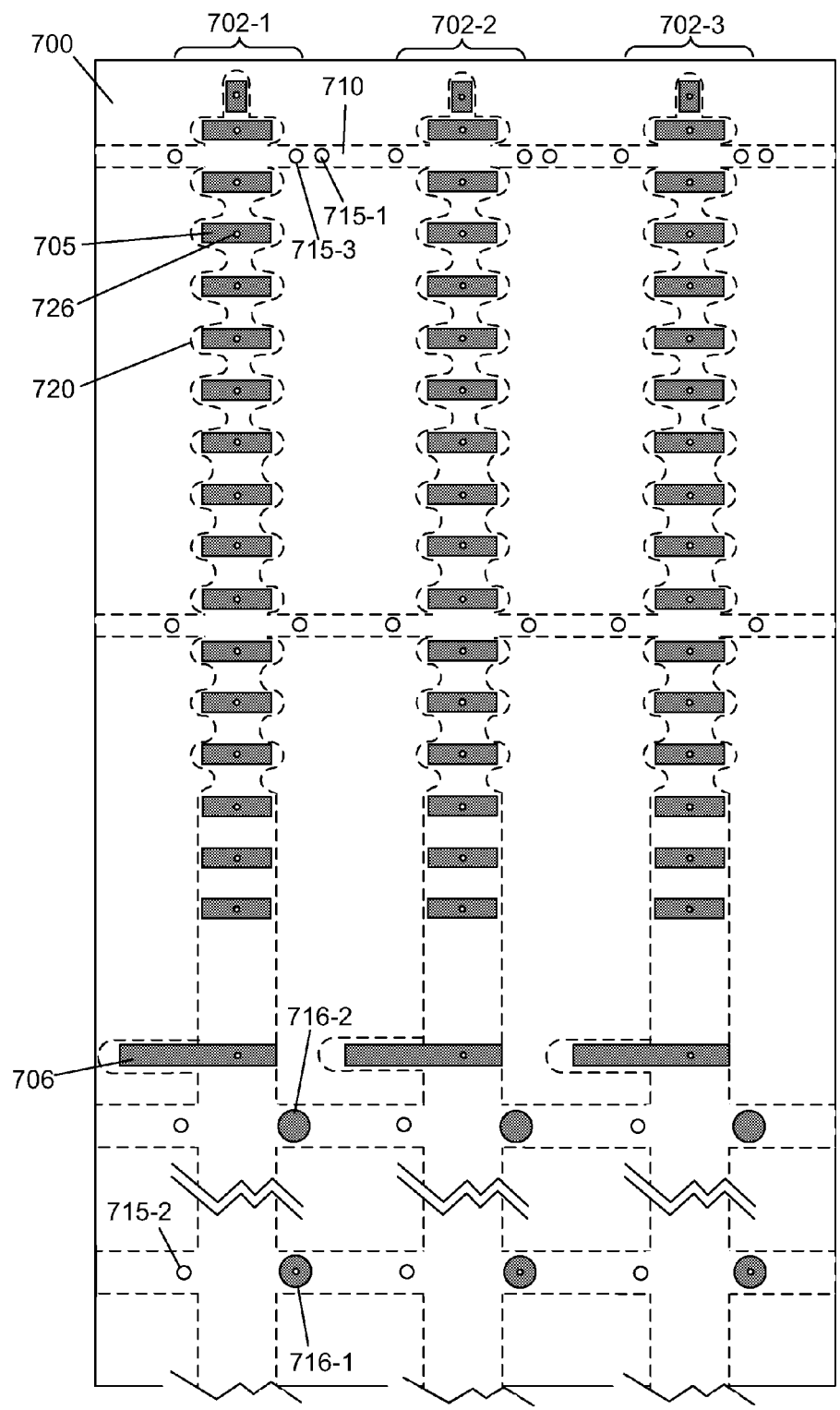

FIG. 7A shows a circuit substrate (700) upon which three implantable circuits (702-1, 702-2, 702-3) will be formed. The circuit substrate (700) may be any of a number of materials, including flexible polymer material and/or a thermoplastic material. A number of electrodes (705, 706) are formed on the upper face of the circuit substrate (700). These electrodes (705, 706) may include stimulating electrodes (705), ring electrodes (706), and other electrodes. In this example, the electrodes have through holes (726) that pass through the electrode and the substrate. These through holes (726) will later be used to form vias to connect traces that will be formed on the opposite side of the substrate (700) to the electrodes (705).

The dashed outlines (720) show where the implantable circuits (702) will subsequently be cut out of the circuit substrate (700). In the example shown in FIG. 7A, there are three implantable circuits (702-1, 702-2, and 702-3) laid out together. The nesting of these implantable circuits together allows for multiple electrode arrays to be formed at the same time. This can increase efficiency in the production of the implantable circuits by reducing handling and fixturing times. The combination of two or more implantable circuits that are formed in a single sheet is called a "tray" of implantable circuits. In the example shown in FIGS. 7A and 7B, there are only three implantable circuits in the tray. However, any number of implantable circuits may be included on the tray and formed simultaneously during the processing steps.

The implantable circuits (702) are connected by extensions (710) that extend on either side of the implantable circuits (702). When the implantable circuits are cut out of the substrate in a subsequent operation, they will still be connected by the extensions (710). In this example, the extensions may include a number of apertures (715), electrodes (716) and other features. When the implantable circuits (702) are individually separated, the extensions (710) can be formed into flag extensions or cut entirely from the implantable circuits (702). These flag extensions may serve a number of purposes as described below.

Figure 7B:
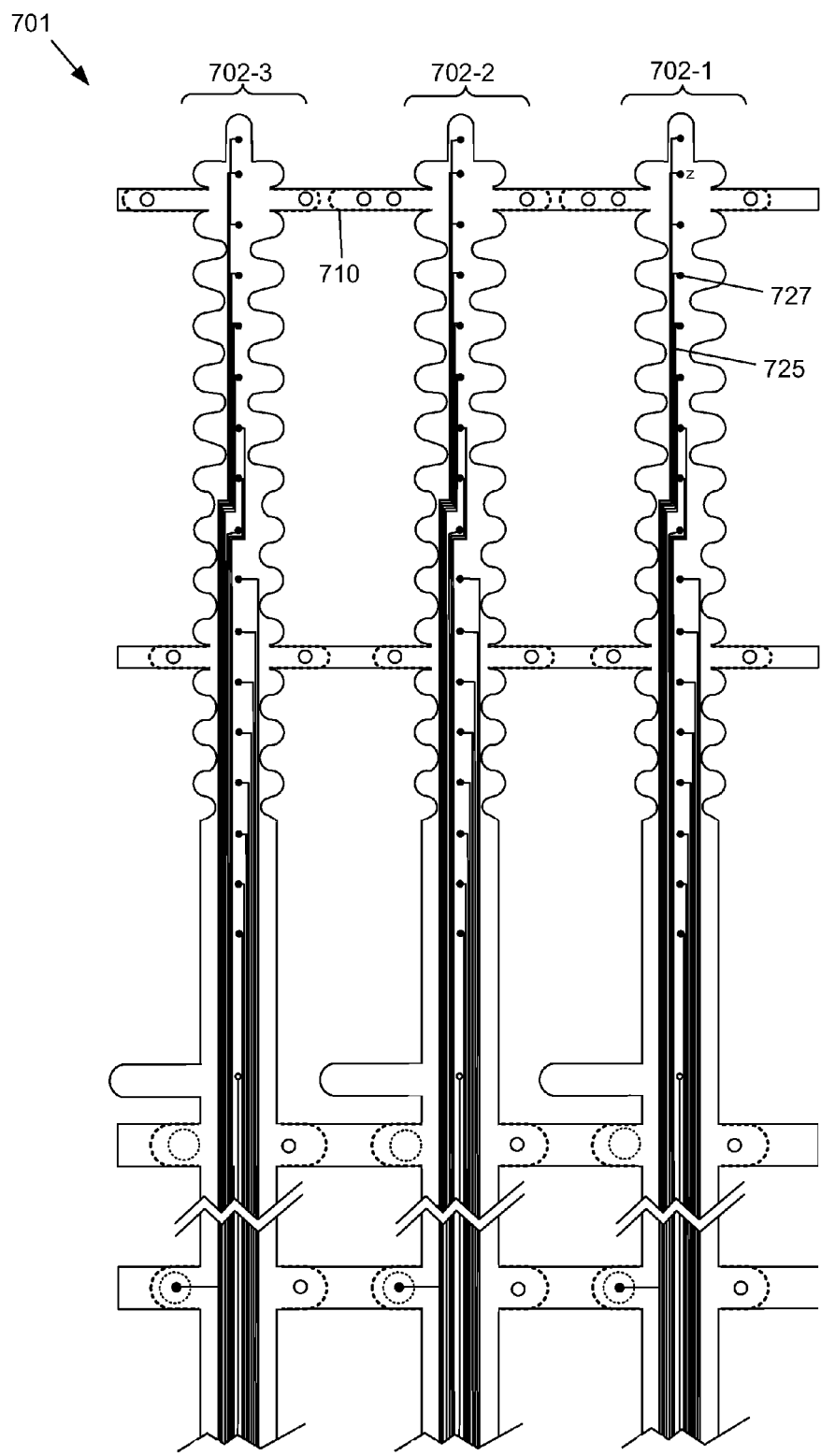

In FIG. 7B, the circuit substrate has been flipped around a vertical axis to show the opposite side of the substrate. In this step of the manufacturing process, a number of traces (725) are formed. During the formation of the traces (725) (or during the formation of the electrodes), the through holes (726, FIG. 7A) are filled to form vias (727). These vias (727) connect traces (725) on the back side of the circuit substrate (700) to the electrodes on the front side of the circuit substrate (700). The electrodes, traces, and vias can be formed from any appropriate material using any appropriate process. For example, the material may be a biologically compatible conductive metal such as gold, platinum, iridium or alloys thereof. The traces, electrode and vias can be formed using a number of processes, including a printing process, lithography, vacuum deposition, electroplating and etching, etc. In some examples, the conductive elements on the substrate may be formed using a combination of processes. For example, the traces may be initially formed using a lithographic process and then thickened using electroplating processes.

FIG. 7B also shows that the circuit substrate has been cut to remove portions of the substrate that are not part of the circuits. This forms the circuit tray (701) with the individual implantable circuits (702) connected by the extensions (710). In this example, there are at least four extensions (710) connecting the implantable circuits (702). The number of extensions (710) can be more or less depending on the specific application, the number of desired flag extensions, and the amount of desired connectivity between the implantable circuits (710).

Figure 8A:
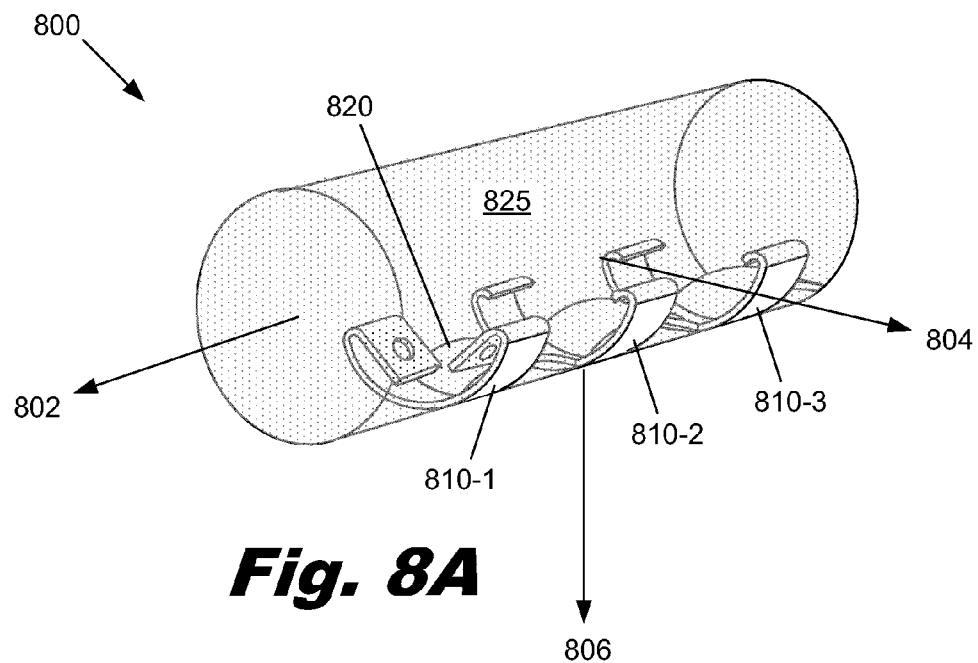
FIGS. 8A and 8B show a partially transparent perspective view and cross sectional view, respectively, of an electrode array that includes electrodes with edges that curl into the interior of a flexible body, according to one example of principles described herein.
Figure 8B:
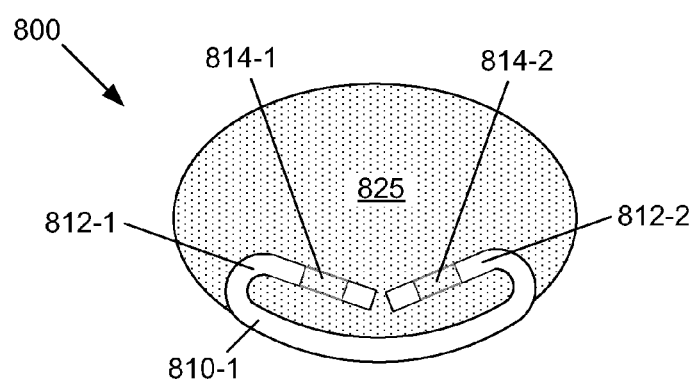

FIG. 7C shows an implantable circuit (702-1) for a cochlear lead that has been separated from the tray (701, FIG. 7B) by cutting the extensions (710, FIG. 7A). The extensions (710, FIG. 7B) then become flag extensions (730) that extend outward from the central body (701) of the implantable circuit (702-1). The flag extensions (730) are integral parts of the circuit (702-1) and are formed out of the circuit substrate (700, FIG. 7A). In this example, there are eight flag extensions (730-1 through 730-8). A first flag extension (730-1) includes two apertures (715-1, 715-3) can be used alignment and for mechanical overlocking. One example of mechanical overlocking using flag extensions is illustrated in FIGS. 8A and 8B.

Figure 7D:
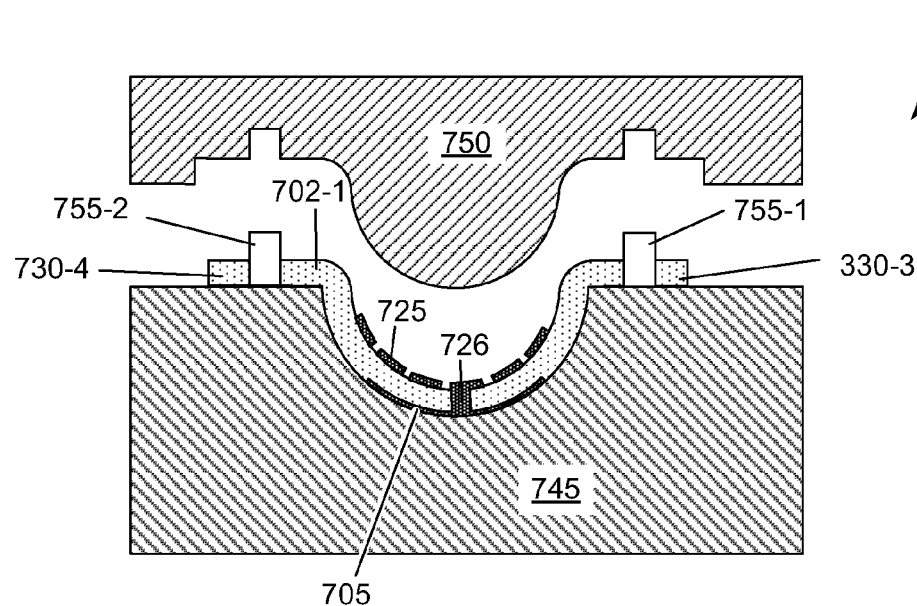
Figure 7E:
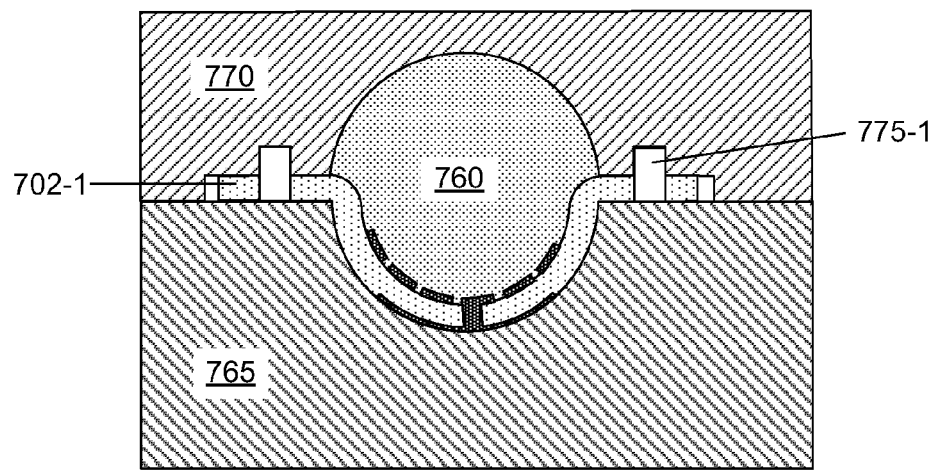

The second, third, and fourth flag extensions (730-2, 730-3, 730-4) include through apertures (e.g. 715-2) that are used for alignment during subsequent operations (see FIGS. 7D and 7E). These flag extensions are removed from the cochlear lead after their alignment functions have been performed. The fifth and seventh flag extensions (730-5, 730-7) are used both for alignment and as a surgical anchor point for the cochlear lead. The sixth flag extension does not have a through aperture but includes a marker electrode (716-2). The marker electrode allows a surgeon to visually determine a correct insertion depth of the cochlear lead into the tissue. The eighth flag extension (730-8) includes an electrode (716-1) connected to a trace (725, FIG. 7B). The electrode (716-1) serves as a contact pad for a subsequently attached ring electrode.

For purposes of illustration, only a few examples of flag extensions are shown. A cochlear lead or other implantable lead may include a variety of different flag extensions and there may be any number of flag extensions in a given design. For example, in some designs there may be flag extensions that extend from both ends of each stimulating electrode that are used to mechanically overlock the electrode into a flexible body (see e.g. FIGS. 8A, 8B).

FIG. 7D shows the implantable circuit (702-1) placed in a thermoforming mold (745, 750). The view of the circuit (702-1) is taken along the section line A-A shown in FIG. 7C. In this example, the circuit (702-1) includes a thermoplastic that can be formed into a predetermined shape through the application of heat and pressure. The thermoforming mold includes a lower mold (745) and a mating upper mold (750). The circuit (702-1) is aligned to the lower mold (745) by placing apertures in the flag extensions (730-3, 730-4) over pins (755) of other alignment features protruding from the lower mold (745). The molds (745, 750) and circuit (702-1) are then heated to a desired temperature and the upper mold (750) is pressed down into the lower mold (745). This forms the circuit (702-1) into the desired shape. During this process, the circuit (702-1) is secured by the pins (755) passing through apertures in the flag extensions (730-3, 730-4). In some implementations, the heating of the circuit (702-1) is not uniform. For example, the center portion of the circuit (702-1) containing the traces (725), vias (727) and electrodes (705) may be heated while the flag extensions (730-3, 730-4) are not heated or are heated to a much lower temperature. In one implantation, the center portion of the circuit (702-1) may be heated above the glass transition temperature of the thermoplastic, while the flag extensions (730-3, 730-4) are not heated above the glass transition temperature. Thus, when the upper mold (710) is brought down into the lower mold (705), the center portion of the circuit (702-1) deforms while the flag extensions (730-3, 730-4) remain more dimensionally stable. The circuit (702-1) is then cooled below the glass transition temperature and removed from the thermoforming mold (745, 750) by pulling the circuit (702-1) upward to withdraw the pins (755) from the apertures in the flag extensions (730-3, 730-4). The circuit (702-1) then retains its thermoformed shape.

FIG. 7E shows the thermoformed circuit (702-1) placed into a liquid injection mold (765, 770). The liquid injection mold includes a lower mold (765) with pins (775-2) that fit into the alignment apertures in the flag extensions. This secures the thermoformed circuit (702-1) in place. The upper mold (770) is secured over the lower mold (765), creating a cavity that is filled with a flexible encapsulant such as silicone to form a flexible body (760). The combination of the flexible body (760) and the thermoformed circuit (702-1) form an implantable lead. The circuit (702-1) provides the electrical functions of the implantable lead and the flexible body (760) improves the mechanical characteristics of the implantable lead. For example, the flexible body (760) smooths the contours of the circuit (702-1) to eliminate edges and corners that may cause tissue irritation. The flexible body (760) may also reduce the tendency of the implantable lead to kink during insertion.

The discussion and illustrations above are only illustrative examples of implantable leads that include flag extensions. A variety of other configurations and materials could be used. For example, the circuit may not include thermoplastic, but may be formed on a flexible substrate. The flexible encapsulant may then be formed around the flexible substrate to hold it in the desired shape. In other implementations, the circuit may include a number of sub-layers that are bonded together. For example the circuit may include both a flexible layer and a thermoplastic layer.

FIG. 7F is a flow chart of a method (780) for forming an implantable cochlear lead. The method includes forming a circuit on a circuit substrate, the circuit substrate comprising a thermoplastic (step 785). The circuit may be many of a variety of circuits including circuits that include an array of implantable electrodes. In some examples, there may be multiple apertures and electrodes. The circuit substrate is cut to form a first flag extension having an aperture passing through the circuit substrate (step 790). As described above, there may be multiple apertures in a single flag extension and multiple flag extensions.

The circuit substrate is then aligned in a thermoforming mold by inserting a first alignment feature through the aperture (step 795). For example, the first alignment feature may be a pin or other shaped protrusion. The circuit substrate is then thermoformed into a predetermined geometry (step 797). The technique of aligning the circuit substrate using apertures in flag extensions can be used in a variety of manufacturing operations including thermoforming, liquid injection molding, lithography, cutting, etc. Using features on flags for alignment has a number of advantages, including the advantage that the flag can be located on a portion of the circuit substrate that is away from the location on the circuit substrate that the operation is taking place.

Where the circuit substrate undergoes multiple manufacturing steps, the flags can be used for alignment in the subsequent steps as well. For example, the circuit substrate may be removed from the thermoforming mold and then aligned in a liquid injection mold by inserting a second alignment feature through apertures in one or more flag extensions. The flag extensions hold the circuit substrate in place while liquid is injected into the liquid injection mold and cured.

Another advantage of using flag extensions for alignment and to secure the circuit substrate in place is that the flag extensions may not be part of the final product. Thus, there are fewer concerns about damaging the flags during the manufacturing process if they are to be eventually removed from the product. For example, high clamping forces may be used to secure the flags in place without particular concern about whether or not the clamping forces compress the flag. After all the manufacturing processes using the flag for alignment and securing the circuit in place are complete, the flag extension may be severed from the circuit substrate.

Other advantages of incorporating flags in the manufacturing process include using the flags to hold multiple circuits together during the early steps of manufacturing. This is shown in FIG. 7A and FIG. 7B. The flags can be cut to separate the circuits in subsequent operations. The flags can then be used for alignment of individual circuits as described above.

Additionally, flag extensions may be thermoformed so that a portion of the second flag extension extends into an interior portion of the flexible body. As the flexible body is formed, it encapsulates portion of the second flag extension to mechanically overlook the second flag extension in the flexible body. One example of extensions that are used for mechanical over locking is given below in FIGS. 8A and 8B.

FIGS. 8A-8B show an alternative implementation of a cochlear electrode array (800). In this example, the electrodes (810) include curled left and right edges. This curl directs the extensions from the lateral sides of the electrodes (810) into the interior of the flexible body (345). The overhang of the curl allows the silicone that makes up the flexible body (345) to more securely grip the electrodes (810), thereby preventing the electrodes (810) from separating from the flexible body (345). Arched intermediate sections (820) join the electrodes (810). These electrodes (810) and arched intermediate sections (820) may be part of the thermoformed circuit.

FIG. 8A also shows three orthogonal axes that can be used to define curvature of a thermoformed circuit (400, FIG. 6A) or other elements in a cochlear electrode array (800). A longitudinal axis (802) is parallel to the major longitudinal axis of the cochlear electrode array (800). A normal axis (806) is normal to the center of the electrode surface. An axis (804) is orthogonal to both the longitudinal axis and the normal axis. When the cochlear electrode array (800) is inserted into a cochlear duct, the longitudinal axis (802) will generally point up the cochlear duct. The normal axis (806)

will typically point toward the modiolus of the cochlea, and the orthogonal axis (804) will point up/down toward the basilar membrane. The orthogonal axis (804) is substantially parallel to an axis along a centerline passing through the middle of the modiolus. In general, the cochlear ducts can be described as spiraling around the modiolus centerline.

Thus, in this example the electrodes (810) contain a primary curvature about the longitudinal axis (802). The primary curvature has a relatively constant radius that matches the radius of the outer surface of the electrode array/flexible body (825). The electrodes (810) also include a secondary curvature about an axis parallel to the longitudinal axis (802) with a much smaller radius so that the edges of the electrodes (810) extend inward into the interior of the flexible body (825). Thus, in this example, the electrodes (810) each include a left edge and a right edge that fold or curl into the interior of the cochlear electrode array (800) and are surrounded by the flexible body (825). The folded edges may have a variety of shapes and sizes. In some examples, the folded edges may include holes through which the silicone can be molded to mechanically overlook the electrodes in place. The arched intermediate portions (820) in this example have curvatures about axes parallel to the orthogonal axis (804). These curvatures provide a number of benefits as described above.

FIG. 8B shows a cross sectional view of an cochlear electrode array (800) that includes a curled left edge (812-1) and a curled right edge (812-2) with holes (814-1, 814-2) that pass through the electrode substrate. As shown in the figure, the silicone passes through the holes and mechanically overlooks the electrode (810-1) in place within the flexible body (825).

Figure 9A:
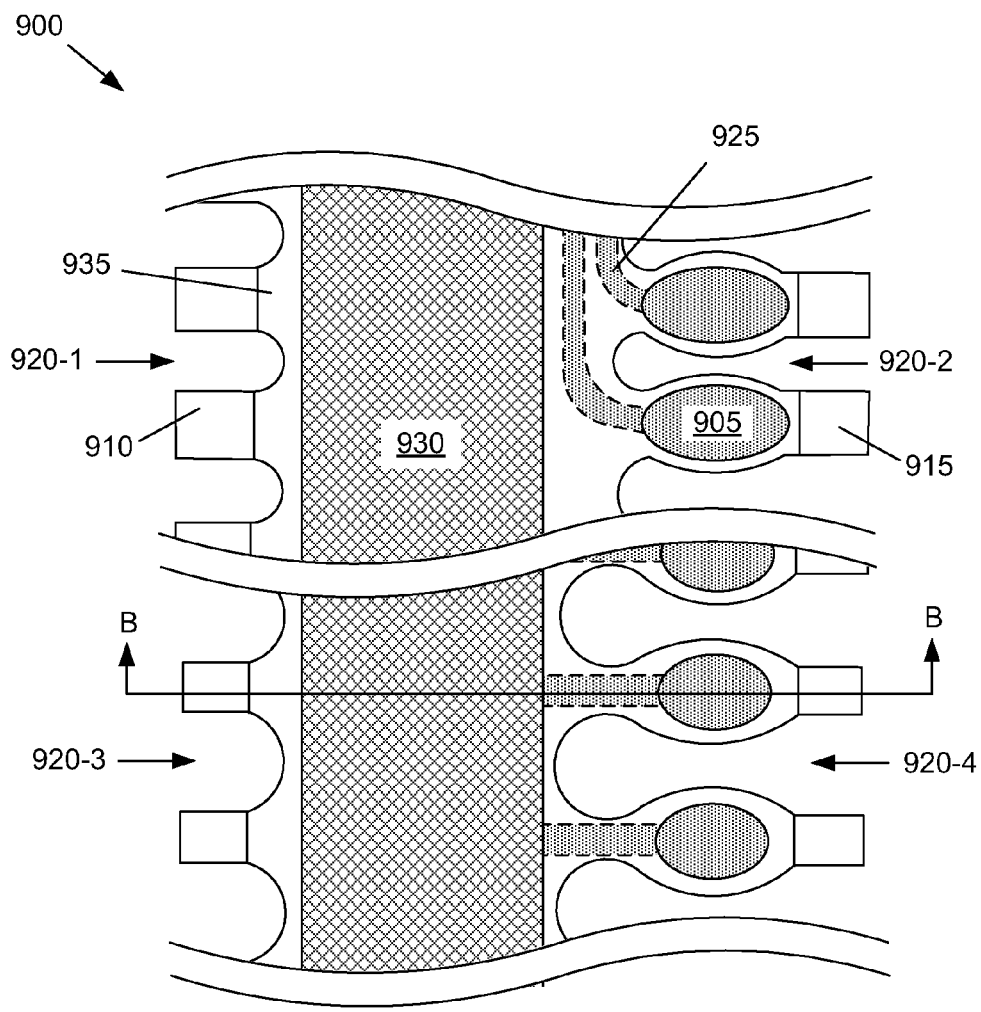
FIG. 9A is a plane/planar view of a multilayer circuit, according to one example of principles described herein.

FIG. 9A is a plane/planar view of a flexible circuit (900) to be used to form a cochlear electrode array (195, FIG. 2B). In this example, the flexible circuit (900) includes a flexible substrate (935) with traces (925) and electrodes (905) formed on its surfaces. The traces (925) and electrodes (905) may be formed on the same side or opposing sides of the flexible substrate (935). The flexible substrate (935) is laminated to a thermoplastic layer (950, FIG. 9B). The flexible substrate (935) may cover an entire surface of the thermoplastic layer (950, FIG. 9B) or may cover only part of the surface of the thermoplastic layer (950, FIG. 9B). In this example the flexible substrate (935) and thermoplastic layer (950, FIG. 9B) are formed to include cutouts (920-2, 920-4) between each of the electrodes (905). These cutouts (920-2, 920-4) may vary in size to produce the desired amount of flexibility in the cochlear electrode array. This flexibility may vary along the length of the cochlear electrode array.

A number of tabs (915) extend from the electrodes (905). Matching tabs (910) are formed on the opposite side of the flexible circuit (900). These tabs may be joined to form rings around exterior of the cochlear electrode array. These matching tabs (910) are also separated by cutouts (920-1, 920-3). These cutouts (920-1, 920-3) may or may not be the same size or shape as the corresponding cutouts (920-2, 920-4) on the opposite edge of the flexible circuit (900). By selectively adjusting the size of the cutouts along the edges, the shape into which the resulting cochlear array bends can be controlled. For example, if the size of the cutouts on the left side are larger (or otherwise more flexible) than the cutouts on the right side, the cochlear array will tend to bend out of plane. Thus, the cutouts can be tailored so that the cochlear electrode array will assume or tend to assume the desired curvature within the cochlea, including an ascending spiral configuration.

A friction reducing area (930) is disposed on the upper surface of the flexible substrate (935). This friction reducing area (930) may take a variety of forms, including texturing of the flexible substrate (935) and/or deposition of an additional layer. For example, the flexible substrate (935) could be textured by imprinting, etching, laser forming or other technique. Illustrative principles and examples related to surface features that reduce friction are described in U.S. patent application Ser. No. 12/781,137, entitled "Cochlear Electrode Array" filed May 17, 2010, which issued as U.S. Pat. No. 8,880,193 and is incorporated herein by reference in its entirety. Additionally or alternatively, a layer may be added over the flexible substrate (935) to form the friction reducing area (930). This layer may include lubricants and/or pharmaceutical products. The layer may also be textured and may include one or more sub-layers. The friction reducing area (930) is exposed in the cochlea and reduces friction between the cochlear electrode array and the interior of the cochlear duct. Illustrative principles and examples of lubricating layers, drugs, drug impregnated polymers, and other layers/structures are described in U.S. patent application Ser. No. 12/202,134, entitled "Minimizing Trauma During and After Insertion of a Cochlear Lead" filed Aug. 29, 2008, which issued May 29, 2013 as U.S. Pat. No. 8,190,271 and is incorporated herein by reference in its entirety.

Figure 9B:
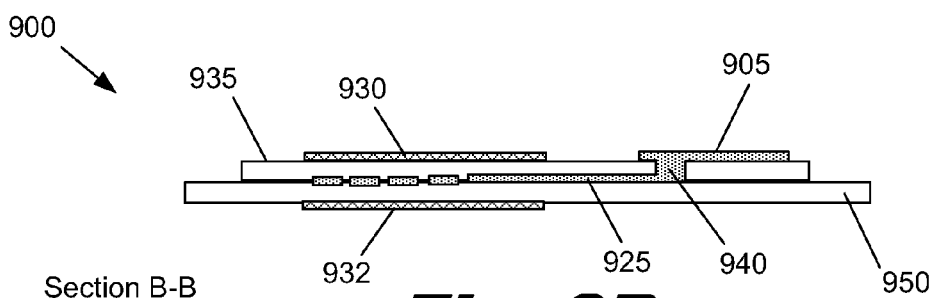
FIG. 9B is a cross sectional view of a multilayer circuit, according to one example of principles described herein.

FIG. 9B is a cross section of the flexible circuit (900, FIG. 9A) showing the various layers. The cross section is taken along section line B-B as shown in FIG. 9A. As discussed above, traces (925), vias (940), and electrodes (905) may be formed on the substrate (935) to provide electrical stimulation to cochlear tissues. A thermoplastic layer (950) is laminated to the substrate (935) and covers the traces (925). The friction reducing area (930) is deposed on the upper surface of the circuit (900). An additional textured area/ lubricant layer (932 may be disposed on the bottom surface of the thermoplastic layer (950). This textured area/lubricant layer (932) will be on the interior of a lumen and will reduce friction between the thermoformed circuit and a stylet inserted into the lumen. The textured area/lubricant layer (932) will also protect the circuit from abrasion/damage by the stylet.

Figure 9C:
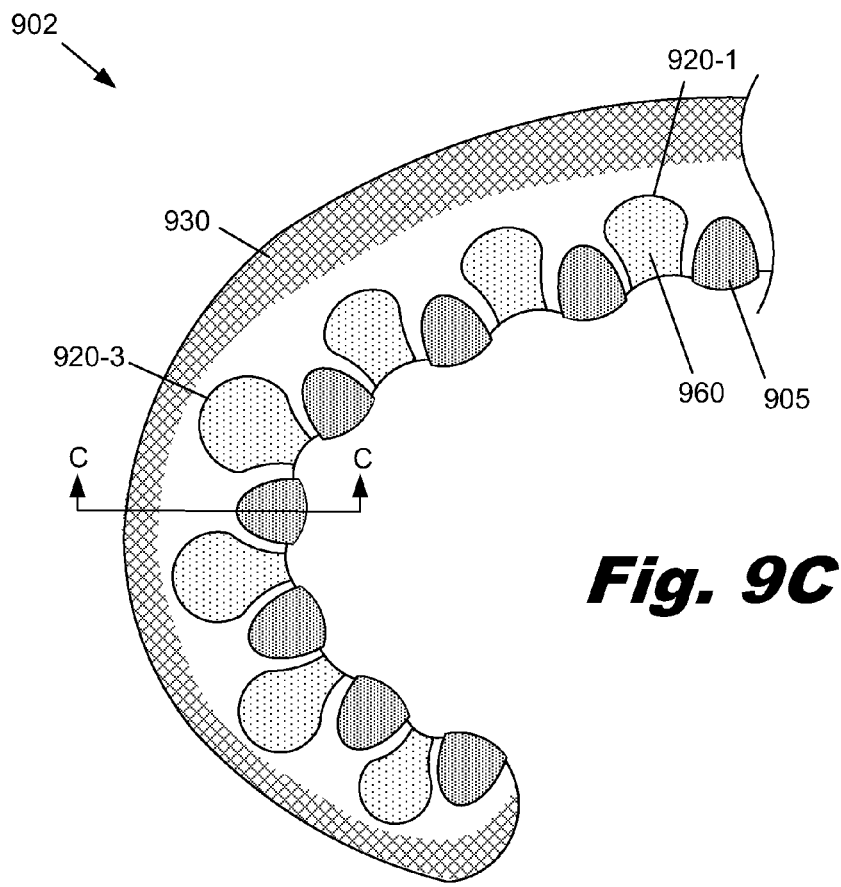
FIG. 9C is a top view of a portion of an electrode array created by thermoforming the multilayer circuit of FIG. 9B, according to one example of principles described herein.

FIG. 9C shows the exterior of a cochlear electrode array (902) that incorporates the flexible circuit (900) shown in FIGS. 9A and 9B. The electrodes (905) have been thermoformed with a three dimensional protruding surface and the cutouts (920) have been filled with silicone (960). For example, the cutouts (920) and portions of the interior of the circuit may be filled with silicone (960) using liquid injection molding. As discussed above, the cutouts (920) may vary in size, thereby providing varying flexibility along the length of the cochlear electrode array (902). Cutouts may be larger between distal electrodes and smaller between proximal electrodes so that a distal portion of the cochlear lead is more flexible than a proximal portion of the cochlear lead. For example, the cutout labeled 920-1 is significantly smaller than the cutout labeled 920-3. Because silicone (960) can be significantly more flexible than the circuit layers, the cochlear electrode array (902) tends to bend where the cutouts (920) are found. The textured area/ lubrication layer (930) is shown on an exterior of the cochlear electrode array (902) so that the textured area/ lubrication layer (930) will contact the lateral wall of the cochlear duct and allow the cochlear lead to side smoothly into the cochlear duct.

Figure 9D:
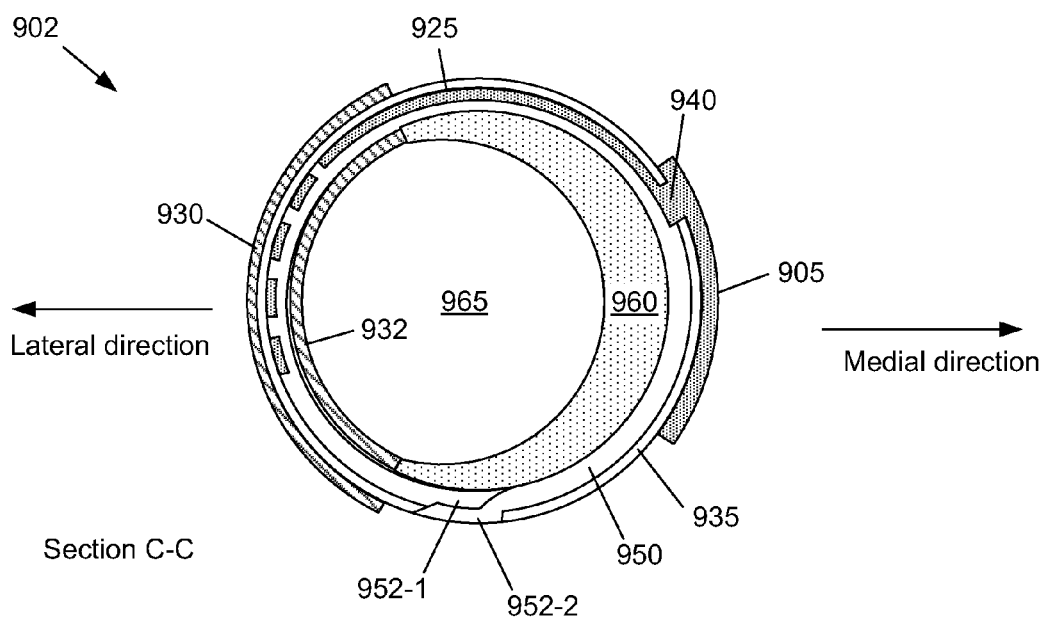
FIG. 9D is a cross sectional view of the electrode array of FIG. 9C, according to one example of principles described herein.

FIG. 9D is a cross sectional view of the cochlear electrode array (902) shown in FIG. 9C at line C-C. This view shows that the circuit (900, FIG. 9B) is wrapped into a tube with the tabs (952) on the opposites of the circuit being joined. As discussed above the circuit includes traces (925), vias (940), and electrodes (905). The layers in the circuit include a substrate (935) and a thermoplastic layer (950). The exterior texture/lubrication layer (930) is on the lateral outside surface of the cochlear electrode array (902). As discussed above, silicone (960) is used to fill the cutouts (920, FIG. 9C) and to define a lumen (965) in the interior of the cochlear electrode array (902). On the lateral interior side of the lumen (965), the interior texture/lubrication layer (932) prevents abrasion and binding of the stylet with the lumen (965).

Figure 10A:
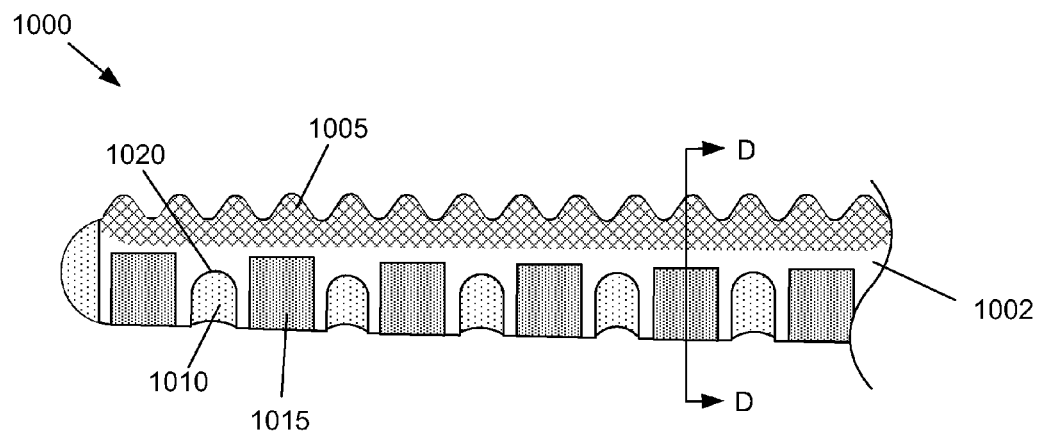
FIGS. 10A-10C show electrode arrays with a corrugated surface, according to one example of principles described herein.
Figure 10B:
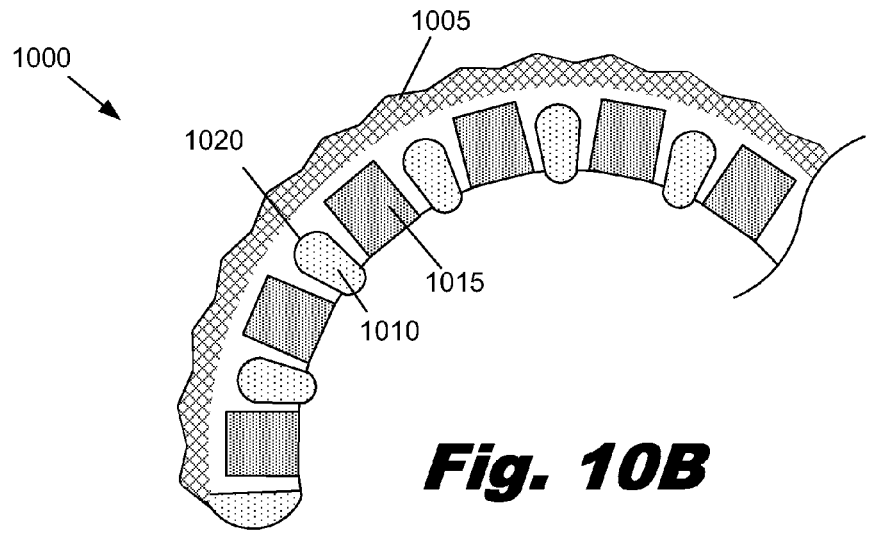
Figure 10C:
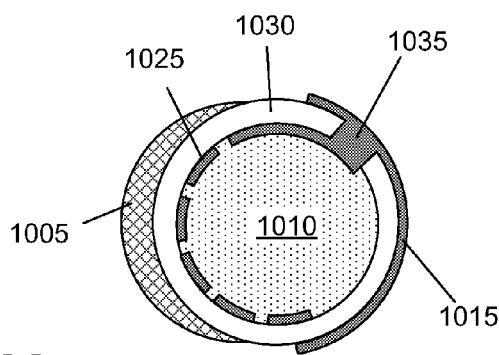

FIGS. 10A-10C show an electrode array (1000) that includes a corrugated surface (1005). FIG. 10A shows the electrode array (1000) that has been made by thermoforming a circuit (1002). The electrode array (1000) includes a number of electrodes (1015) extending along one side of the array. Cutouts (1020) are formed between the electrodes (1015). Silicone or other flexible material (1010) has been used to fill the electrode array (1000) and cutouts (1020). In some examples, the silicone may be liquid injected and cured while the electrode array is in a curled configuration. Consequently, when the electrode array is straightened as shown in FIG. 10A, the cutouts may open slightly, thereby placing tension on the silicone in the cutouts. This may produce a tendency for the electrode array to resume its previous curled configuration.

The surface of the electrode array that will contact the lateral (outside) wall of the cochlear duct has been corrugated. This may be accomplished in a variety of ways, including corrugating a layer that is disposed over the flexible circuit. Additionally or alternatively, the circuit may be formed with the corrugations. For example, during a thermoforming operation, a portion of the circuit could be stretched and molded to form the corrugations. The corrugations may serve a variety of functions, including reducing the amount of surface contact area between the electrode array and the interior of the cochlea. This can significantly reduce the amount of friction between the electrode array and the cochlea. Additionally, the corrugations may allow this side of the electrode array to stretch/elongate so that the electrode array is more flexible.

FIG. 10B shows the electrode array (1000) in a bent configuration. As the electrode array (1000) bends, the corrugations (1005) can flatten and allow the outside surface of the electrode array to lengthen. At the same time, the cutouts (1020) on the opposite side of the electrode array (1000) are becoming narrower. The silicone or other flexible material (1010) in the cutouts (1020) deforms to allow the cutouts (1020) to close in a controlled manner. The electrodes (1015) retain their shape during bending.

FIG. 10C is a cross sectional diagram of the electrode array (1000 FIG. 10A) along the section line D-D. In this example, the thermoformed circuit (1002, FIG. 10A) includes a single layer thermoplastic substrate (1030) with traces (1025) formed on the interior side and the electrodes (1015) formed on the exterior side. A via (1035) connects the traces to the circuit. A corrugated surface (1005) is formed on/in one side of the substrate. During the thermoforming process, the circuit is formed into a tube by joining two edges. In FIGS. 10A-10C, the edges are shown as being seamlessly joined. As discussed above, this joint may be formed in a variety of ways, including pressing the two edges together under heat and pressure. In this example, silicone or other flexible material (1010) fills the interior of the tube.

The embodiments described above are only examples used to illustrate the principles described. A variety of other embodiments could be used to implement the principles. For example, the circuit could be formed on a single thermoplastic substrate without any additional thermoplastic layer. The thermoplastic substrate could be folded to provide additional area for traces and/or circuitry. Illustrative principles and examples related to folded circuits are described in International Pat. App. No. PCT/US2012/025485, entitled "Wire Constructs" published on Nov. 15, 2012 as International Pat. Pub. No. WO2012154256 which is incorporated herein by reference in its entirety. A variety of additional features could be added to the cochlear implant, including sensors, pharmaceutical delivery devices, and actuators. For example, the silicone disposed within the cutouts could be used as electro-active polymer actuators. By changing the size/shape of the silicone in the cutouts the overall shape of the electrode array could be altered. In addition to silicone, other types of electro-active polymer or other actuators could be used. Additionally, the silicone may be impregnated with a variety of drugs, including steroids and anti-inflammatory drugs. Illustrative principles and examples of drugs, drug impregnated polymers, and other deliver methods are described in U.S. patent application Ser. No. 12/202,134, entitled "Minimizing Trauma During and After Insertion of a Cochlear Lead" which was incorporated by reference above.

Additionally, the lead body may be formed as an integral part of this process. For example, the circuits could be extended to form the conductors that pass through the lead body and connect to the processor. The circuit could terminate in connector pads or a connector. Illustrative examples of connector pads and connectors are given in International Pat App. No. PCT US2011/053742, filed Sep. 28, 2011, entitled "Modular Biomedical Implants," which published as International Pat. Pub. No. WO2013048396 and is incorporated herein by reference in its entirety. Conductors passing through the lead body could be thermoformed into a variety of shapes, including wave shapes or spiral shapes. Examples of processes for manufacturing flexible electrode arrays, lead bodies, connector pads/processor interfaces, and other features are described in U.S. patent application Ser. No. 12/338,758, entitled "Microcircuit Cochlear Electrode Array and Method of Manufacture" filed on Dec. 18, 2008, which issued as U.S. Pat. No. 8,250,745, and U.S. patent application Ser. No. 12/727,160, also entitled "Microcircuit Cochlear Electrode Array and Method of Manufacture", filed on Mar. 18, 2010, which issued as U.S. Pat. No. 8,332,052, which applications are incorporated herein by reference in their entirety.

Figure 11:
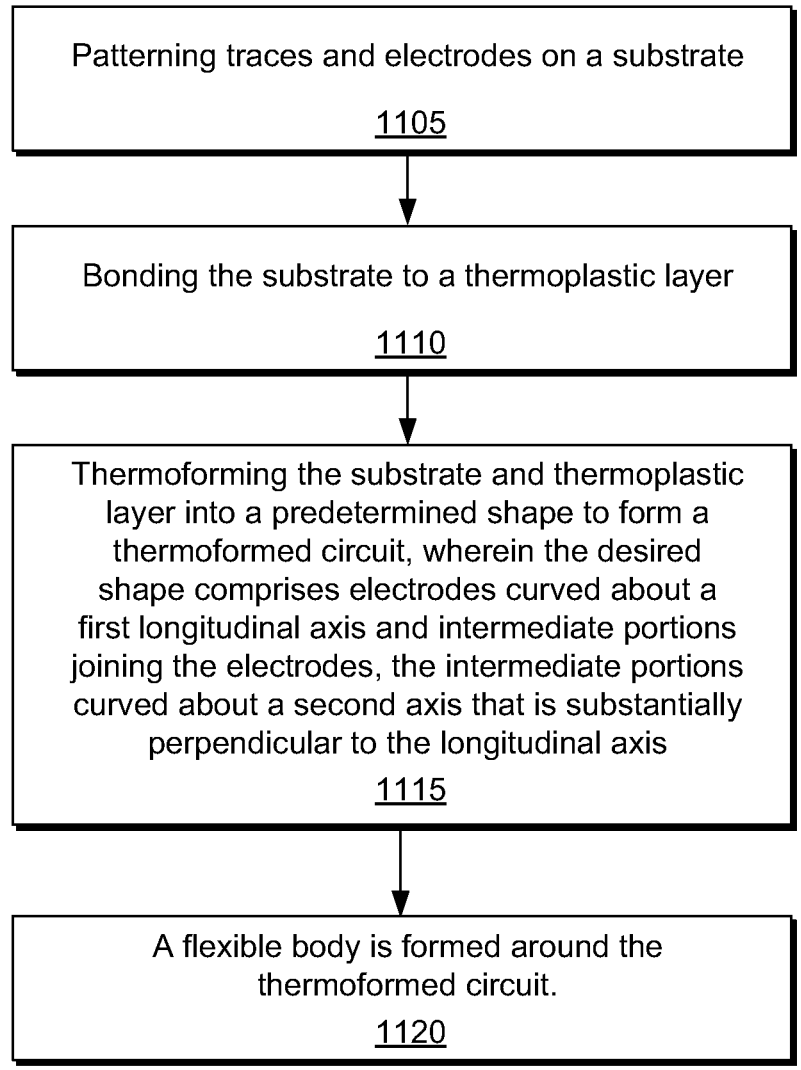
FIG. 11 is a flowchart of a method for forming a cochlear electrode array, according to one example of principles described herein.

FIG. 11 is a flowchart of a method (1100) for forming a cochlear lead. The method includes patterning traces and electrodes on a substrate (step 1105) and bonding the substrate to a thermoplastic layer (step 1110). The substrate and the thermoplastic layer are thermoformed into a predetermined shape to form a thermoformed circuit. The thermoformed circuit includes electrodes curved about a first longitudinal axis and intermediate portions joining the electrodes, the intermediate portions curved about a second axis that is substantially orthogonal to the longitudinal axis (step 1115). For example, the thermoforming may include pressing the substrate and thermoplastic layer into a heated mold cavity. Thermoforming may also include joining a first edge and a second edge of the circuit to form a continuous tube. In some implementations, the thermoforming process may include joining a first edge of the thermoplastic layer to a second edge of the thermoplastic layer to form a tube or ring.

For example, a first tab extending from a first side of an electrode may be joined with a second tab from a second side of the electrode so that each electrode is disposed on a continuous circular ring as shown in FIGS. 9C and 9D. Other examples include forming the tube at the proximal end of the electrode array as shown in FIGS. 6A and 6B. A flexible body is formed around the thermoformed circuit and thermoplastic layer (step 1120). For example, silicone may be liquid injection molded around/in the thermoformed circuit and thermoplastic layer.

FIG. 11 is only one example of a method for forming a cochlear lead that includes a thermoformed circuit. A variety of other approaches could be used. For example, the steps shown in FIG. 11 may be reordered, merged, deleted or separated. Additionally, a variety of steps may be added. For example, after forming the flexible body, silicone flash may be removed from the surfaces of the electrodes using laser ablation. Additionally, a friction reducing layer may be disposed on a first side of the circuit and a second friction reducing layer may be disposed on the thermoplastic layer. The thermoforming of the circuit and thermoplastic layer forms the circuit/thermoplastic layer into a segmented tube with a central lumen such that the friction reducing layer on the first side of the circuit is configured to reduce friction between a lateral wall of a cochlear duct. The second friction reducing layer is configured to reduce friction with a stylet inserted into the lumen.

The preceding description has been presented only to illustrate and describe examples of the principles described. This description is not intended to be exhaustive or to limit these principles to any precise form disclosed. Many modifications and variations are possible in light of the above teaching.

What is claimed is:

1. A cochlear lead comprising:
    a thermoformed circuit comprising:
        a substrate;
        electrodes formed on the substrate, wherein the electrodes are shaped to curve around a longitudinal axis of the cochlear lead;
        traces formed on the substrate and connected to the electrodes; and
        intermediate sections between the electrodes, wherein, when the lead is straight prior to implantation in a cochlea, at least a portion of the intermediate sections are curved around an axis that is orthogonal to the longitudinal axis.

2. The cochlear lead of claim 1, wherein the thermoformed circuit further comprises a basal extension formed into a tube, an interior of the tube forming a lumen to receive a stylet.

3. The cochlear lead of claim 1, wherein proximal intermediate sections curve around the longitudinal axis and distal intermediate sections curve around the axis that is orthogonal to the longitudinal axis.

4. The cochlear lead of claim 1, wherein the electrodes comprise a curled left edge and a curled right edge, wherein the curled left edge and the curled right edge curl into an interior of the cochlear lead and are surrounded by a flexible encapsulant.

5. The cochlear lead of claim 1, wherein the electrodes comprise a three dimensional surface with a compound curvature about two different axes.

6. The cochlear lead of claim 1, further comprising cutouts between the electrodes to increase flexibility of the cochlear lead, wherein the cutouts are larger between distal electrodes and smaller between proximal electrodes to make a distal portion of the cochlear lead more flexible than a proximal portion of the cochlear lead and wherein the cutouts on a first side of the cochlear lead are larger than the cutouts on a second side of the cochlear lead to make the cochlear lead bend into an ascending spiral.

7. The cochlear lead of claim 6, further comprising flexible silicone that fills cutouts between electrodes.

8. The cochlear lead of claim 7, wherein the flexible silicone filling the cutouts is in tension when the cochlear lead is straight.

9. The cochlear lead of claim 1, further comprising tabs extending from the electrodes, in which the tabs are joined to form rings around a central lumen of the cochlear lead.

10. The cochlear lead of claim 1, wherein the substrate comprises:
    a flexible substrate in which the electrodes are formed on a first surface of the flexible substrate and traces are formed on a second surface of the flexible substrate; and
    a thermoplastic layer adhered to the thermoformed circuit to cover the traces.

11. A method comprising:
    patterning traces and electrodes on a substrate;
    bonding the substrate to a thermoplastic layer;
    thermoforming the substrate and thermoplastic layer into a predetermined shape to form a thermoformed circuit, wherein the predetermined shape comprises electrodes curved around a first longitudinal axis and intermediate portions joining the electrodes, the intermediate portions curved about a second axis that is orthogonal to the longitudinal axis when the circuit is straightened along the longitudinal axis; and
    liquid injection molding silicone around the thermoformed circuit.

12. The method of claim 11, further comprising removing silicone flash from the electrodes using a laser operation, wherein the laser operation also forms a predetermined surface texture on the electrodes.

13. The method of claim 11, wherein thermoforming comprises:
    aligning the circuit and thermoplastic layer by passing an alignment feature in a thermoforming mold through an aperture in a flag extension formed in the thermoplastic layer; and
    pressing the substrate and thermoplastic layer into a mold cavity.

14. The method of claim 11, wherein thermoforming comprises joining a first edge of the thermoplastic layer to a second edge of the thermoplastic layer to form a continuous tube.

15. The method of claim 11, wherein thermoforming comprising joining a first tab extending from a first side of an electrode with a second tab extending from a second side of the electrode.

* * * * *